US007442551B2

(12) United States Patent
Kaleko et al.

(10) Patent No.: US 7,442,551 B2
(45) Date of Patent: *Oct. 28, 2008

(54) LENTIVIRAL PACKAGING CONSTRUCTS

(75) Inventors: Michael Kaleko, Potomac, MD (US); Tianci Luo, Clarksville, MD (US); Ivan Plavec, Sunnyvale, CA (US); Janet Lynn Douglas, San Francisco, CA (US)

(73) Assignee: Novartis AG, Basel (CH)

( * ) Notice: Subject to any disclaimer, the term of this patent is extended or adjusted under 35 U.S.C. 154(b) by 151 days.

This patent is subject to a terminal disclaimer.

(21) Appl. No.: 11/428,118

(22) Filed: Jun. 30, 2006

(65) Prior Publication Data

US 2007/0010017 A1 Jan. 11, 2007

Related U.S. Application Data

(63) Continuation of application No. 10/097,002, filed on Mar. 13, 2002, now Pat. No. 7,070,993.

(60) Provisional application No. 60/275,275, filed on Mar. 13, 2001.

(51) Int. Cl.
| | |
|---|---|
| C12N 15/63 | (2006.01) |
| C12N 15/64 | (2006.01) |
| C12N 15/867 | (2006.01) |
| C12N 5/10 | (2006.01) |
| A61K 48/00 | (2006.01) |
| C07H 21/02 | (2006.01) |
| C07H 21/04 | (2006.01) |

(52) U.S. Cl. .................. 435/455; 435/69.1; 435/325; 435/320.1

(58) Field of Classification Search .................. None
See application file for complete search history.

(56) References Cited

U.S. PATENT DOCUMENTS

| 5,380,830 | A | 1/1995 | Gonda | |
|---|---|---|---|---|
| 5,994,136 | A | 11/1999 | Naldini et al. | |
| 6,207,455 | B1 | 3/2001 | Chang | 435/457 |
| 6,277,633 | B1 | 8/2001 | Olsen | 435/320.1 |
| 6,864,085 | B2 | 3/2005 | Luo et al. | 435/320.1 |
| 7,070,993 | B2 * | 7/2006 | Kaleko et al. | 435/325 |
| 2003/0104611 | A1 | 6/2003 | Johnston | 435/320.1 |

FOREIGN PATENT DOCUMENTS

| WO | WO 96/19573 | 6/1996 |
|---|---|---|
| WO | WO 97/46687 | 12/1997 |
| WO | WO 98/39463 | 9/1998 |
| WO | WO 01/44458 | 6/2001 |
| WO | WO 01/68835 | 9/2001 |
| WO | WO 02/072851 | 9/2002 |

OTHER PUBLICATIONS

PCT International Search Report for PCT/EP02/02807 dated Jun. 6, 2003.
Agarwal, et al., "Scaffold Attachment Region-Mediated Enhancement of Retroviral Vector Expression in Primary T Cells", *J. Virology*, 72(5):3720-3728 (May 1998).
Auten, et al., "Effect of Scaffold Attachment Region on Transgene Expression in Retrovirus Vector-Transduced Primary T Cells and Macrophages", *Human Gene Therapy*, 10:1389-1399 (May 20, 1999).
Berkowitz, et al., "Construction and Molecular Analysis of Gene Transfer Systems Derived from Bovine Immunodeficiency Virus", *Journal of Virology*, 75(7):3371-3382 (Apr. 2001).
Beyer, et al., "Oncoretrovirus and Lentivirus Vectors Pseudotyped with Lymphocytic Choriomeningitis Virus Glycoprotein: Generation, Concentration, and Broad Host Range", *J. Virology*, 76(3):1488-1495 (Feb. 2002).
Carroll, et al., "A Human Immunodeficiency Virus Type 1 (HIV-1)-Based Retroviral Vector System Utilizing Stable HIV-1 Packaging Cell Lines", *J. Virology*, 68(9):6047-6051 (Sep. 1994).
Dang, et al., "Human Beta Interferon Scaffold Attachment Region Inhibits De Novo Methylation and Confers Long-Term, Copy Number-Dependent Expression to a Retroviral Vector", *J. Virology*, 74(6):2671-2678 (Mar. 2000).
Douglas, et al., "Efficient Human Immunodeficiency Virus-Based Vector Transduction of Unstimulated Human Mobilized Peripheral Blood CD34+ Cells in the SCID-hu Thy/Liv Model of Human T Cell Lymphopoieses", *Human Gene Therapy*, 12:401-413 (Mar. 1, 2001).
Farson, et al., "Lentikat3™: Creation and Characterization of High Titer Third Generation Lentivirus Producer Clones in a VSV.G Packaging Cell Line", *Molecular Therapy*, 5(5), No. 940 (May 2002).
Farson, et al., "A New-Generation Stable Inducible Packaging Cell Line for Lentiviral Vectors", *Human Gene Therapy*, 12:981-997 (May 20, 2001).
Garvey, et al., "Nucleotide Sequence and Genome Organization of Biologically Active Proviruses of the Bovine Immunodeficiency-line Virus", *Virology*, 175(2):391-409 (Apr. 1990).
Gossen, et al., "Tight Control of Gene Expression in Mammalian Cells by Tetracycline-Responsive Promoters", *Proc. Natl. Acad. Sci. USA*, 89:5547-5551 (Jun. 1992).
Haselhorst, et al., "Development of Cell Lines Stably Expressing Human Immunodeficiency Virus Type 1 Proteins for Studies in Encapsidation and Gene Transfer", *Journal of General Virology*, 79:231-237 (1998).
Junker, et al., "Intracellular Expression of Human Immunodeficiency Virus Type 1 (HIV-1) Protease Variants Inhibits Replication of Wild-Type and Protease Inhibitor-Resistant HIV-1 Strains in Human T-Cell Lines", *J. Virology*, 70(11):7765-7772 (Nov. 1996).
Kafri, et al., "A Packaging Cell Line for Lentivirus Vectors", *J. Virology*, 73(1):576-584 (Jan. 1999).
Kaplan, et al., "Human Immunodeficiency Virus Type 1 Gag Proteins are Processed in Two Cellular Compartments", *Proc. Natl. Acad. Sci. USA*, 88:4528-4532 (May 1991).

(Continued)

*Primary Examiner*—David Guzo
(74) *Attorney, Agent, or Firm*—MDIP LLC

(57) ABSTRACT

The present invention provides novel lentiviral packaging constructs that are useful for the establishment of stable packaging cell lines and producer cell lines. In particular, the present invention provides novel packaging cell lines that are capable of constitutively expressing high levels of lentiviral proteins.

17 Claims, 3 Drawing Sheets

OTHER PUBLICATIONS

Kirillov, et al., "A Role for Nuclear NF-kappaB in B-Cell-Specific Demethylation of the Igkappa Locus", *Nature Genetics*, 13(4):435-441 (1996).

Klehr, et al., "Scaffold-Attached Regions From the Human Interferon beta Domain Can Be Used to Enhance the Stable Expression of Genes Under the Control of Various Promoters", *Biochemistry*, 30(5):1264-1270 (Feb. 5, 1991).

Konvalinka, et a., "An Active-Site Mutation in the Human Immunodeficiency Virus Type 1 Proteinase (PR) Causes Reduced PR Activity and Loss of PR-Mediated Cytotoxicity without Apparent Effect on Virus Maturation and Infectivity", *J. Virology*, 69(11):7180-7186 (Nov. 1995).

Korber, et al., "Limitations of a Molecular Clock Applied to Considerations of the Origin of HIV-1", *Science*, 280:1868-1871 (Jun. 19, 1998).

Krausslich, et al., "Analysis of Protein Expression and Virus-Like Particle Formation in Mammalian Cell Lines Stably Expressing HIV-1 gag and env Gene Products With or Without Active HIV Proteinase", *Virology*, 192(2):605-617 (Feb. 1993).

Mochizuki, et al., "High-Titer Human Immunodeficiency Virus Type 1-Based Vector Systems for Gene Delivery into Nondividing Cells", *Journal of Virology*, 72(11):8873-8883 (Nov. 1998).

Naldini, et al., "In Vivo Gene Delivery and Stable Transduction of Nondividing Cells by a Lentiviral Vector", *Science*, 272:263-267 (1996).

Ory, et al., "A Stable Human-Derived Packaging Cell Line for Production of High Titer Retrovirus/Vesicular Stomatitis Virus G Pseudotypes", *Proc. Natl. Acad. Sci. USA*, 93:11400-11406 (Oct. 1996).

Pacchia, et al., "An Inducible Packaging Cell System for Safe, Efficient Lentiviral Vector Production in the Absence of HIV-1 Accessory Proteins", *Virology*, 282:77-86 (2001).

Rogel, et al., "The Human Immunodeficiency Virus Type 1 vpr Gene Prevents Cell Proliferation During Chronic Infection", *J. Virology*, 69(2):882-888 (Feb. 1995).

Rosé, et al., "Defining the Level of Human Immunodeficiency Virus Type 1 (HIV-1) Protease Activity Required for HIV-1 Particle Maturation and Infectivity", *Journal of Virology*, 69(5):2751-2758 (May 1995).

Srinivasakumar, et al., "The Effect of Viral Regulatory Protein Expression on Gene Delivery by Human Immunodeficiency Virus Type 1 Vectors Produced in Stable Packaging Cell Lines", *J. Virology*, 71(8):5841-5848 (Aug. 1997).

Sutton, et al., "Human Immunodeficiency Virus Type 1 Vectors Efficiently Transduce Human Hematopoietic Stem Cells", *J. Virology*, 72(7):5781-5788 (Jul. 1998).

Zufferey, et al., *Nature Biotechnology*, 15:871-875 (1997).

Kotsopoulou et al., *J. Virology*, 74(10)4839-4852, 2000.

Haas et al., *Current Biology*, 6(3)315-324, 1996.

* cited by examiner

Recoded BIV Gag/Pol Expression Construct

Poly(A)

SEQUENCE LISTING

```
<160> NUMBER OF SEQ ID NOS: 17

<210> SEQ ID NO 1
<211> LENGTH: 29
<212> TYPE: PRT
<213> ORGANISM: Human immunodeficiency virus

<400> SEQUENCE: 1

Pro Gln Val Thr Leu Trp Gln Arg Pro Leu Val Thr Ile Lys Ile Gly
1               5                   10                  15

Gly Gln Leu Lys Glu Ala Leu Leu Asp Thr Gly Ala Asp
            20                  25

<210> SEQ ID NO 2
<211> LENGTH: 29
<212> TYPE: PRT
<213> ORGANISM: Bovine immunodeficiency virus

<400> SEQUENCE: 2

Ser Tyr Ile Arg Leu Asp Lys Gln Pro Phe Ile Lys Val Phe Ile Gly
```

```
1               5                  10                 15
Gly Arg Trp Val Lys Gly Leu Val Asp Thr Gly Ala Asp
            20                 25
```

<210> SEQ ID NO 3
<211> LENGTH: 29
<212> TYPE: PRT
<213> ORGANISM: Human immunodeficiency virus

<400> SEQUENCE: 3

```
Pro Gln Val Thr Leu Trp Gln Arg Pro Leu Val Thr Ile Lys Ile Gly
1               5                  10                 15
Gly Gln Leu Lys Glu Ala Leu Leu Asp Ser Gly Ala Asp
            20                 25
```

<210> SEQ ID NO 4
<211> LENGTH: 29
<212> TYPE: PRT
<213> ORGANISM: Bovine immunodeficiency virus

<400> SEQUENCE: 4

```
Ser Tyr Ile Arg Leu Asp Lys Gln Pro Phe Ile Lys Val Phe Ile Gly
1               5                  10                 15
Gly Arg Trp Val Lys Gly Leu Val Asp Ser Gly Ala Asp
            20                 25
```

<210> SEQ ID NO 5
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: Primer A

<400> SEQUENCE: 5
aattgcaggg ccccctaggaa aaa                                      23

<210> SEQ ID NO 6
<211> LENGTH: 25
<212> TYPE: DNA
<213> ORGANISM: Artificial Sequence
<220> FEATURE:
<221> NAME/KEY: misc_feature
<222> LOCATION: (1)..(25)
<223> OTHER INFORMATION: Primer B

<400> SEQUENCE: 6
tctgctcctg aatctaatag cgctt                                     25

<210> SEQ ID NO 7
<211> LENGTH: 25
<212> TYPE: DNA
<213> ORGANISM: Artificial Sequence
<220> FEATURE:
<221> NAME/KEY: misc_feature
<223> OTHER INFORMATION: Primer C

<400> SEQUENCE: 7
aagcgctatt agattcagga gcaga                                     25

<210> SEQ ID NO 8
<211> LENGTH: 24
<212> TYPE: DNA
<213> ORGANISM: Artificial Sequence

```
<220> FEATURE:
<221> NAME/KEY: misc_feature
<222> LOCATION: (1)..(24)
<223> OTHER INFORMATION: primer D

<400> SEQUENCE: 8
ccatgtaccg gttctttag aatc                                              24

<210> SEQ ID NO 9
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: primer CTE1

<400> SEQUENCE: 9
cggggtacca cctcccctgt gagctag                                          27

<210> SEQ ID NO 10
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: primer CTE2

<400> SEQUENCE: 10
tgctctagag acacatccct cggaggc                                          27

<210> SEQ ID NO 11
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: primer GAG5

<400> SEQUENCE: 11
ccgctcgaga tgaagagaag ggagttagaa                                       30

<210> SEQ ID NO 12
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: primer POL3

<400> SEQUENCE: 12
ccgctcgagt cacgaactcc catcttggat                                       30

<210> SEQ ID NO 13
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Primer A

<400> SEQUENCE: 13
gggttagtag actctgga                                                    18
```

```
<210> SEQ ID NO 14
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: primer A

<400> SEQUENCE: 14
gcccgggtcg actctaga                                                   18

<210> SEQ ID NO 15
<211> LENGTH: 4427
<212> TYPE: DNA
<213> ORGANISM: Artificial Sequence
<220> FEATURE:
<221> NAME/KEY: misc_feature
<222> LOCATION: (1)..(4427)
<223> OTHER INFORMATION: Sequence of recoded gag/pol

<400> SEQUENCE: 15
atgaagcgga gagagctgga gaagaaactg aggaaagtgc gcgtgacacc tcaacaggac       60
aagtactata ccatcggcaa cctgcagtgg gccatccgca tgatcaacct gatgggcatc      120
aagtgcgtgt gcgacgagga atgcagcgcc gctgaggtcg ccctgatcat cacccagttt      180
agcgccctcg acctggagaa ctcccctatc cgcggcaagg aagaggtggc catcaagaat      240
accctgaagg tgttttggag cctgctggcc ggatacaagc tgagagcac cgagaccgcc       300 ctgggatact gggaagcctt cacctacaga gagagggaag ctagagccga caaggaggga      360
gagatcaaga gcatctaccc tagcctgacc cagaacaccc agaacaagaa acagaccagc      420
aatcagacaa cacccagag cctgcccgct atcaccacac aggatggcac ccctcgcttc       480
gaccccgacc tgatgaagca gctgaagatc tggtccgatg ccacagagcg caatggagtg      540
gacctgcatg ccgtgaacat cctgggagtg atcacagcca acctggtgca agaagagatc      600
aagctcctgc tgaatagcac acccaagtgg cgcctggacg tgcagctgat cgagagcaaa      660
gtgagagaga aggagaacgc ccaccgcacc tggaagcagc atcaccctga ggctcccaag      720
acagacgaga tcattggaaa gggactgagc tccgccgagc aggctaccct gatcagcgtg      780
gagtgcagag agaccttccg ccagtgggtg ctgcaggctg ccatggaggt cgcccaggct      840
aagcacgcca cacccggacc tatcaacatc atcaaggcc taaggaacc ctacaccgac        900 ttcatcaacc gcctggtggc tgccctggaa ggaatggccg ctcccgagac acaaaggag       960 tacctcctgc agcacctgag catcgaccac gccaacgagg actgtcagtc catcctgcgc     1020
cctctgggac ccaacacacc tatggagaag aaactggagg cctgtcgcgt ggtgggaagc     1080
cagaagagca gatgcagtt cctggtggcc gctatgaagg aaatggggat ccagtctcct     1140
attccagccg tgctgcctca cacacccgaa gcctacgcct cccaaacctc agggcccgag     1200
gatggtagga gatgttacgg atgtgggaag acaggacatt tgaagaggaa ttgtaaacag     1260
caaaaatgct accattgtgg caaacctggc caccaagcaa gaaactgcag gtcaaaaaac     1320
gggaagtgct cctctgcccc ttatgggcag aggagccaac cacagaacaa ttttcaccag     1380
agcaacatga gttctgtgac ccatctgca ccccctctta tattgatta cagacaacagc      1440 ctttttataa ggtgttcatt ggcggccgct gggtgaaggg actggtggac acaggcgctg     1500
acgaggtggt gctgaagaac atccactggg accgcatcaa aggctaccct ggaacaccca     1560
tcaagcagat cggcgtgaac ggcgtgaacg tggctaagcg caaaacacat gtggagtgga      1620
```

```
gattcaaaga caagaccggc atcattgacg tcctcttcag cgacacacct gtgaacctgt    1680
ttggcagaag cctgctcaga tccatcgtga cctgctttac cctgctggtg cacaccgaga    1740
agatcgagcc actgcctgtg aaggtgcgcg ccctggacc taaggtgcca caatggcccc     1800
tgaccaagga gaaataccag gccctgaagg agatcgtgaa ggacctgctg gccgagggaa    1860
agatcagcga agctgcctgg gacaacccctt acaacacacc cgtgttcgtg atcaagaaga   1920
aaggcaccgg ccgctggcgc atgctgatgg acttccgcga gctgaataag atcaccgtga    1980
aaggccaaga gttcagcaca ggactcccctt atccacccgg catcaaggag tgtgagcacc   2040
tgaccgccat cgacatcaag gacgcctact tcaccatccc tctgcacgag gacttcagac    2100
ccttcacagc cttcagcgtg gtcccagtga accgcgaggg ccccatcgag cgcttccagt    2160
ggaacgtcct gcctcaaggc tgggtgtgct cccctgccat ctaccagacc acaacccaga    2220
agatcattga gaacatcaag aagagccatc ccgacgtgat gctgtatcag tacatggatg    2280
acctcctgat tggcagcaat cgcgatgacc acaagcagat cgtgcaggag atcagagaca    2340
agctgggcag ctatggcttc aagacacccg acgagaaagt gcaggaagag cgcgtgaagt    2400
ggatcggctt cgagctgaca cctaagaaat ggagattcca gcctaggcaa ctgaagatca    2460
agaacccact gaccgtgaac gaactccagc agctggtcgg caactgtgtg tgggtgcagc    2520
ccgaggtgaa gatccctctg tacccactga ccgatctgct ccgcgacaag accaacctgc    2580
aggaaaagat ccagctgaca cccgaggcca tcaagtgcgt ggaagagttc aacctgaagc    2640
tgaaagatcc cgagtggaag gacagaattc gcgaaggagc cgagctggtg atcaagatcc    2700
aaatggtccc tcgcggcatc gtgttcgacc tgctgcaaga cggcaatcct atctggggag    2760
gcgtgaaagg actgaactac gaccacagca acaagatcaa gaagatcctg cgcaccatga    2820
acgagctgaa ccgcaccgtg gtgatcatga ccggacgcga agctagcttt ctcctgcctg    2880
gatccagcga ggattgggag gccgccctgc agaaggaaga gagcctgacc caaatctttc    2940
ccgtgaagtt ctaccgccat agctgtagat ggacaagcat ctgtggaccc gtccgcgaga    3000
acctgaccac ctactatacc gacggcggga agaaaggaaa gacagctgcc gcagtgtact    3060
ggtgtgaagg aagaactaag agcaaagtgt tccctggaac caatcaacag gctgagctga    3120
aggcaatctg catggctctg ctggacggac ctcccaagat gaacatcatc accgacagcc    3180
gctacgctta tgagggcatg agagaggaac ctgagacctg ggctcgcgag ggcatctggc    3240
tggagattgc aaagatcctg ccattcaagc aatacgtcgg agtgggctgg gtccctgctc    3300
acaaaggcat tggaggcaat accgaggctg acgaaggagt gaagaaagcc ctggagcaaa    3360
tggcaccatg ttcccctccc gaggctatcc tgctcaaacc tggcgagaag caaaacctgg    3420
agaccggcat ctacatgcaa ggcctgagac tcagagcttc ctgccccgc gctgacctcc     3480
ctgtcgcaat cactgcacc atggtggact ccgagctgca gctccaactg ctgaacatcg      3540
gcaccgagca cattcgcatc cagaaggacg aggtgttcat gacatgcttc ctggagaaca    3600
tccctagcgc caccgaagac cacgagagat ggcacacatc cccagacatc ctggtccgcc    3660
agttccacct gcccaagcgc atcgccaagg agatcgtcgc ccgctgccag gagtgcaaga    3720
gaaccacaac ctcccccagtg cgcggcacca accctagagg acgcttcctg tggcagatgg   3780
acaacacaca ctgaacaaa accatcattt gggtcgcagt ggagactaac agcggactgg    3840
tggaggctca ggtgattccc gaagagaccg cactgcaagt ggccctgtgt atcctccagc    3900
tgatccaacg ctacaccgtc ctgcacctgc acagcgacaa cggaccctgc ttcacagctc    3960
```

```
accgcatcga gaacctgtgc aagtacctgg gcatcaccaa gacaaccggc attccctaca    4020
atcctcagag ccaaggagtc gtggaaagag cccatcgcga cctgaaggac agactggctg    4080
cctatcaagg cgactgcgag accgtggaag ctgcactgag cctcgccctg gtcagcctga    4140
acaagaagag aggaggcatc ggcggacaca cccctacga gatctatctg agagcgagc     4200 acaccaagta tcaggaccaa ctggagcagc aattcagcaa gcagaagatc gagaaatggt    4260
gctacgtccg caacagacgc aaggagtgga agggccctta caaggtgctg tgggatggcg    4320
acggagctgc agtgatcgag aagagggca agaccgctct gtatccccac cggcacatgc     4380
gcttcatccc acctcccgac agcgatatcc aggacggctc cagctga                  4427
```

<210> SEQ ID NO 16
<211> LENGTH: 561
<212> TYPE: DNA
<213> ORGANISM: Bovine immunodeficiency virus
<220> FEATURE:
<221> NAME/KEY: misc_feature
<222> LOCATION: (1)..(561)
<223> OTHER INFORMATION: Sequence of Rev gene

<400> SEQUENCE: 16

```
atggatcagg acctagaccg cgcggaacgc ggggaaaggg gaggaggatc cgaagaactg     60
cttcaggagg agatcaacga agggaggctg acagccagaa agctttaca aacatggatc     120 aataacgatt ctcctaggta tgttaagaag ctgcgccaag gtcagccaga attaccaaca    180
tctcccggcg gaggaggagg acgggacac agagccagaa agctccccgg cgagaggaga    240
cccggcttct ggaagtctct acgagaattg gttgaacaaa ataggagaaa gcaagaacga    300
cgcctatcgg gtctggacag aagaatacaa cagcttgagg atcttgttcg ccacatgtcg    360
ctgggatctc ctgaccctc aactccttca gcttccgttc tttctgttaa ccctcctgct      420
caaactcctt tgggacatct tccgccacgc tcctatttta aacttaaaag gtggactgt      480 ggggcagggt gggacctcag acaacagca gcccccggac ttcccatatg tgaattggac    540
tggatccagg gaacaaaata a                                              561
```

<210> SEQ ID NO 17
<211> LENGTH: 4427
<212> TYPE: DNA
<213> ORGANISM: Artificial Sequence
<220> FEATURE:
<221> NAME/KEY: misc_feature
<222> LOCATION: (1)..(4427)
<223> OTHER INFORMATION: Sequence of recoded gag/pol with protease
      mutation

<400> SEQUENCE: 17

```
atgaagcgga gagagctgga gaagaaactg aggaaagtgc gcgtgacacc tcaacaggac     60
aagtactata ccatcggcaa cctgcagtgg gccatccgca tgatcaacct gatgggcatc    120
aagtgcgtgt gcgacgagga atgcagcgcc gctgaggtcg ccctgatcat cacccagttt    180
agcgccctcg acctggagaa ctcccctatc cgcggcaagg aagaggtggc catcaagaat    240
accctgaagg tgtttggag cctgctggcc ggatacaagc tgagagcac cgagaccgcc      300 ctgggatact gggaagcctt cacctacaga gagagggaag ctagagccga caaggaggga    360
gagatcaaga gcatctaccc tagcctgacc agaacaccc agaacaagaa acagaccagc     420
aatcagacaa acaccagag cctgcccgct atcaccacac aggatggcac ccctcgcttc    480
gaccccgacc tgatgaagca gctgaagatc tggtccgatg ccacagagcg caatggagtg    540
```

-continued

| | | | |
|---|---|---|---|
| gacctgcatg ccgtgaacat cctgggagtg atcacagcca acctggtgca agaagagatc | 600 |
| aagctcctgc tgaatagcac acccaagtgg cgcctggacg tgcagctgat cgagagcaaa | 660 |
| gtgagagaga aggagaacgc ccaccgcacc tggaagcagc atcaccctga ggctcccaag | 720 |
| acagacgaga tcattggaaa gggactgagc tccgccgagc aggctaccct gatcagcgtg | 780 |
| gagtgcagag agaccttccg ccagtgggtg ctgcaggctg ccatggaggt cgcccaggct | 840 |
| aagcacgcca cacccggacc tatcaacatc atcaaggcc taaggaacc ctacaccgac | 900 |
| ttcatcaacc gcctggtggc tgccctggaa ggaatggccg ctcccgagac acaaaggag | 960 |
| tacctcctgc agcacctgag catcgaccac gccaacgagc actgtcagtc catcctgcgc | 1020 |
| cctctgggac ccaacacacc tatggagaag aaactggagg cctgtcgcgt ggtgggaagc | 1080 |
| cagaagagca agatgcagtt cctggtggcc gctatgaagg aaatggggat ccagtctcct | 1140 |
| attccagccg tgctgcctca cacacccgaa gcctacgcct cccaaacctc agggcccgag | 1200 |
| gatggtagga gatgttacgg atgtgggaag acaggacatt tgaagaggaa ttgtaaacag | 1260 |
| caaaaatgct accattgtgg caaacctggc caccaagcaa gaaactgcag gtcaaaaaac | 1320 |
| gggaagtgct cctctgcccc ttatgggcag aggagccaac cacagaacaa ttttcaccag | 1380 |
| agcaacatga gttctgtgac cccatctgca cccctctta tattagatta gacaaacagc | 1440 |
| cttttataaa ggtgttcatt ggcggccgct gggtgaaggg actggtggac tcaggcgctg | 1500 |
| acgaggtggt gctgaagaac atccactggg accgcatcaa aggctaccct ggaacaccca | 1560 |
| tcaagcagat cggcgtgaac ggcgtgaacg tggctaagcg caaaacacat gtggagtgga | 1620 |
| gattcaaaga caagaccggc atcattgacg tcctcttcag cgacacacct gtgaacctgt | 1680 |
| ttggcagaag cctgctcaga tccatcgtga cctgctttac cctgctggtg cacaccgaga | 1740 |
| agatcgagcc actgcctgtg aaggtgcgcg gccctggacc taaggtgcca caatggcccc | 1800 |
| tgaccaagga gaaataccag gccctgaagg agatcgtgaa ggacctgctg ccgagggaa | 1860 |
| agatcagcga agctgcctgg gacaaccctt acaacacacc cgtgttcgtg atcaagaaga | 1920 |
| aaggcaccgg ccgctggcgc atgctgatgg acttccgcga gctgaataag atcaccgtga | 1980 |
| aaggccaaga gttcagcaca ggactcccctt atccacccgg catcaaggag tgtgagcacc | 2040 |
| tgaccgccat cgacatcaag gacgcctact tcaccatccc tctgcacgag gacttcagac | 2100 |
| ccttcacagc cttcagcgtg gtcccagtga accgcgaggg ccccatcgag cgcttccagt | 2160 |
| ggaacgtcct gcctcaaggc tgggtgtgct cccctgccat ctaccagacc acaacccaga | 2220 |
| agatcattga gaacatcaag aagagccatc ccgacgtgat gctgtatcag tacatggatg | 2280 |
| acctcctgat tggcagcaat cgcgatgacc acaagcagat cgtgcaggag atcagagaca | 2340 |
| agctgggcag ctatggcttc aagacacccg acgagaaagt gcaggaagag cgcgtgaagt | 2400 |
| ggatcggctt cgagctgaca cctaagaaat ggagattcca gcctaggcaa ctgaagatca | 2460 |
| agaacccact gaccgtgaac gaactccagc agctggtcgg caactgtgtg tgggtgcagc | 2520 |
| ccgaggtgaa gatccctctg tacccactga ccgatctgct ccgcgacaag accaacctgc | 2580 |
| aggaaaagat ccagctgaca cccgaggcca tcaagtgcgt ggaagagttc aacctgaagc | 2640 |
| tgaaagatcc cgagtggaag acagaattcg cgaaggagc cgagctggtg atcaagatcc | 2700 |
| aaatggtccc tcgcggcatc gtgttcgacc tgctgcaaga cggcaatcct atctggggag | 2760 |
| gcgtgaaagg actgaactac gaccacagca acaagatcaa gaagatcctg cgcaccatga | 2820 |
| acgagctgaa ccgcaccgtg gtgatcatga ccggacgcga agctagcttt ctcctgcctg | 2880 |
| gatccagcga ggattgggag gccgcccctgc agaaggaaga gagcctgacc caaatctttc | 2940 |

-continued

```
ccgtgaagtt ctaccgccat agctgtagat ggacaagcat ctgtggaccc gtccgcgaga    3000
acctgaccac ctactatacc gacggcggga agaaaggaaa gacagctgcc gcagtgtact    3060
ggtgtgaagg aagaactaag agcaaagtgt tccctggaac caatcaacag gctgagctga    3120
aggcaatctg catggctctg ctggacggac ctcccaagat gaacatcatc accgacagcc    3180
gctacgctta tgagggcatg agagaggaac ctgagacctg ggctcgcgag ggcatctggc    3240
tggagattgc aaagatcctg ccattcaagc aatacgtcgg agtgggctgg gtccctgctc    3300
acaaaggcat tggaggcaat accgaggctg acgaaggagt gaagaaagcc ctggagcaaa    3360
tggcaccatg ttccctccc gaggctatcc tgctcaaacc tggcgagaag caaaacctgg    3420
agaccggcat ctacatgcaa ggcctgagac ctcagagctt cctgccccgc gctgacctcc    3480
ctgtcgcaat cactggcacc atggtggact ccgagctgca gctccaactg ctgaacatcg    3540
gcaccgagca cattcgcatc cagaaggacg aggtgttcat gacatgcttc ctggagaaca    3600
tccctagcgc caccgaagac cacgagagat ggcacacatc cccagacatc ctggtccgcc    3660
agttccacct gcccaagcgc atcgccaagg agatcgtcgc ccgctgccag gagtgcaaga    3720
gaaccacaac ctccccagtg cgcggcacca accctagagg acgcttcctg tggcagatgg    3780
acaacacaca ctggaacaaa accatcattt gggtcgcagt ggagactaac agcggactgg    3840
tggaggctca ggtgattccc gaagagaccg cactgcaagt ggccctgtgt atcctccagc    3900
tgatccaacg ctacaccgtc ctgcacctgc acagcgacaa cggaccctgc ttcacagctc    3960
accgcatcga gaacctgtgc aagtacctgg gcatcaccaa gacaaccggc attccctaca    4020
atcctcagag ccaaggagtc gtggaaagag cccatcgcga cctgaaggac agactggctg    4080
cctatcaagg cgactgcgag accgtggaag ctgcactgag cctcgccctg gtcagcctga    4140
acaagaagag aggaggcatc ggcggacaca caccctacga gatctatctg gagagcgagc    4200
acaccaagta tcaggaccaa ctggagcagc aattcagcaa gcagaagatc gagaaatggt    4260
gctacgtccg caacagacgc aaggagtgga agggcccttta caaggtgctg tgggatggcg    4320
acggagctgc agtgatcgag gaagagggca agaccgctct gtatccccac cggcacatgc    4380
gcttcatccc acctcccgac agcgatatcc aggacggctc cagctga              4427
```

LENTIVIRAL PACKAGING CONSTRUCTS

This application is a Continuation of U.S. patent application Ser. No. 10/097,002, filed Mar. 13, 2002, now U.S. Pat. No. 7,070,993, and claims the benefit under 35 USC §119(e) of U.S. provisional patent application No. 60/275,275, filed Mar. 13, 2001, for "Lentiviral Packaging Constructs." The disclosure of this provisional application is incorporated herein by reference in its entirety.

FIELD OF THE INVENTION

The invention relates to novel lentiviral packaging constructs, stable packaging cell lines, stable producer cell lines and the use thereof for producing recombinant lentiviral vectors in mammalian cells.

BACKGROUND OF THE INVENTION

Lentiviruses are complex retroviruses which, in addition to the common retroviral genes gag, pol and env, contain other genes with regulatory or structural function. The higher complexity enables the lentivirus to modulate the life cycle in the course of latent infection. A typical and well-characterized lentivirus is the human immunodeficiency virus (HIV), however, several animal lentiviruses have been described as well.

Viral vectors derived from lentiviruses are a useful tool for gene delivery. The ability of lentiviral vectors to deliver a gene into a broad range of rodent, primate and human somatic cells makes these vectors well suited for transferring genes to a cell for gene therapy purposes. Lentiviruses can infect terminally differentiated cells that rarely divide, such as neurons and macrophages, which renders them particularly useful for certain gene therapy applications requiring the transduction of non-dividing cells.

For producing recombinant lentiviral vectors packaging cell lines are used which supply in trans the proteins necessary for producing infectious virions. An important consideration in the construction of retroviral packaging cell lines is the production of high titer vector supernatants free of recombinant replication competent retrovirus (RCR). One approach to minimize the likelihood of generating RCR in packaging cells is to divide the packaging functions into at least two constructs, for example, one which expresses the gag and pol gene products and the other which expresses the env gene product. This approach minimizes the ability for co-packaging and subsequent transfer of the two genomes, as well as significantly decreasing the frequency of recombination between the viral genomes in the packaging cell to produce RCR. In the event recombinants arise, mutations or deletions can be configured within the undesired gene products to render any possible recombinants non-functional. In addition, deletion of the 3' LTR on the packaging constructs further reduces the ability to form functional recombinants.

One of the major hurdles encountered in the art when producing a stable lentiviral-based packaging cell line is the inability to maintain high levels of expression of Gag/Pol proteins. This could be due to the inherent toxicity of some of the lentiviral proteins or to diminished protein expression from promoter silencing. Accordingly, packaging systems currently known in the art are either transient packaging systems or employ inducible promoters to minimize toxicity problems (Naldini et al., Science 272:263-267, 1996; Kafri et al., Journal of Virology 73:576-584, 1999). These approaches, however, are disadvantageous because they require considerable effort and time for lentiviral vector production. Furthermore, vector batches obtained from such systems will display a higher variability as compared to batches that would be obtainable from stable packaging cell lines. Furthermore, it is difficult to scale up lentiviral vector production from a transient system.

SUMMARY OF THE INVENTION

The present invention provides novel lentiviral packaging constructs that are useful for the establishment of stable packaging cell lines and producer cell lines. In particular, the present invention provides novel packaging cell lines that are capable of constitutively expressing high levels of lentiviral proteins, such as for example HIV p24 gag protein in the case of a HIV based packaging cell line, or of BIV RT protein in the case of a BIV based packaging cell line.

In one aspect the present invention provides a lentiviral packaging construct comprising a deletion in the lentiviral packaging signal and a portion of the lentiviral pol gene which includes the protease encoding sequence, wherein said protease encoding sequence includes a mutation corresponding to a T26S substitution in the encoded lentiviral protease. In another aspect a stable pre-packaging cell line is provided comprising the packaging construct of the invention.

In a further aspect, a stable packaging cell line comprising the packaging construct of the invention and further comprising a plasmid comprising an env gene is provided, as well as a producer cell line which additionally comprises a lentiviral plasmid vector.

In yet another aspect a lentiviral vector particle obtained from the stable producer cell line of the invention is provided.

Also provided is a method for producing a lentiviral vector particle preparation comprising the steps of transfecting the stable packaging cell line of the invention with a lentiviral plasmid vector, propagating the cell line obtained thereby in a suitable culture medium and obtaining a lentiviral vector particle preparation from the said culture medium.

DESCRIPTION OF THE FIGURES

FIG. 1A shows a series of packaging constructs: PHIVΔΨ; pΔVΔR further having a deletion of vif and vp; pΔVΔR-PR* further having a point mutation in the active site of protease; pΔVΔR-SAR and pΔVΔR-PR*SAR further including the interferon β SAR element. FIG. 1B shows the transfer vector pHLEIP. FIG. 1C shows envelope constructs useful for pseudotyping.

DETAILED DESCRIPTION OF THE INVENTION

Figure 1:
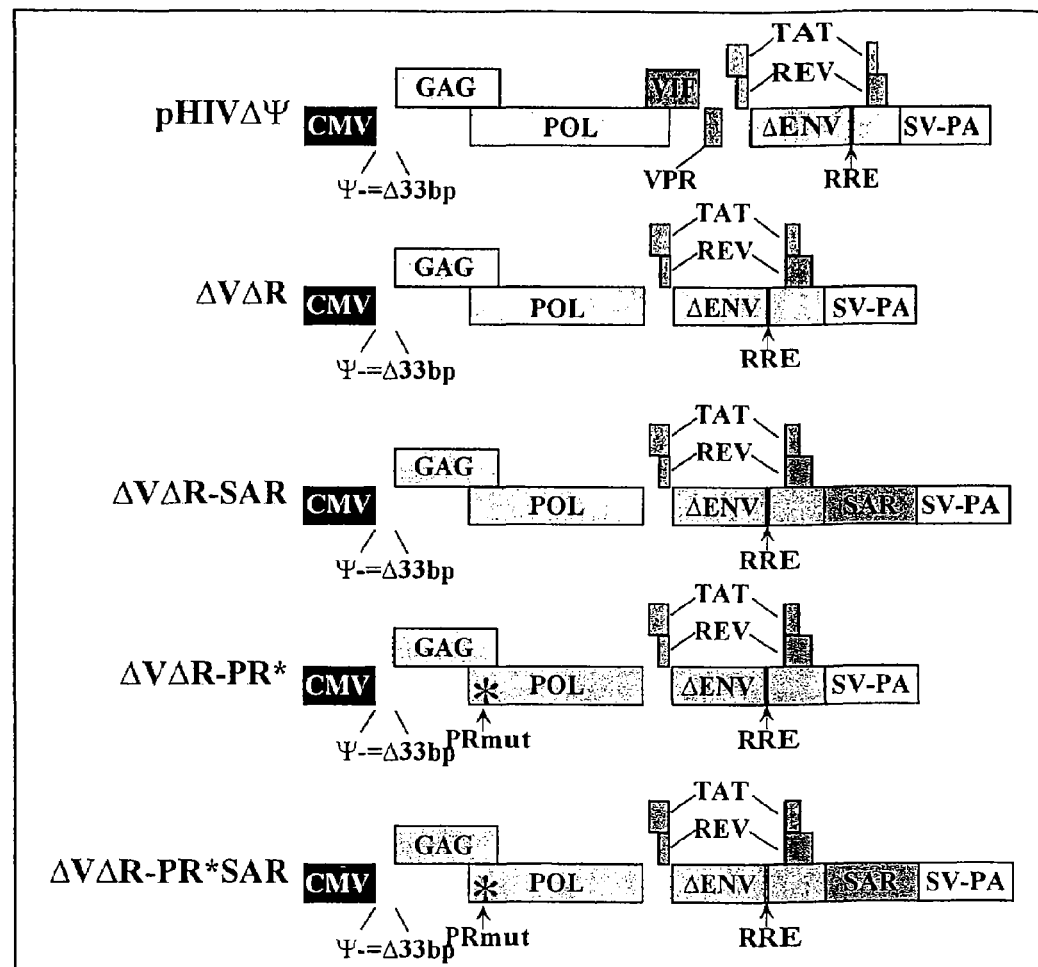
FIG. 1 shows HIV-based vectors of the invention in a schematic view.
Figure 1:
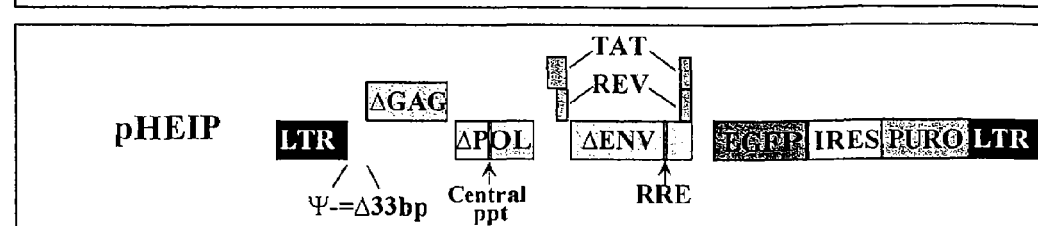
Figure 1:
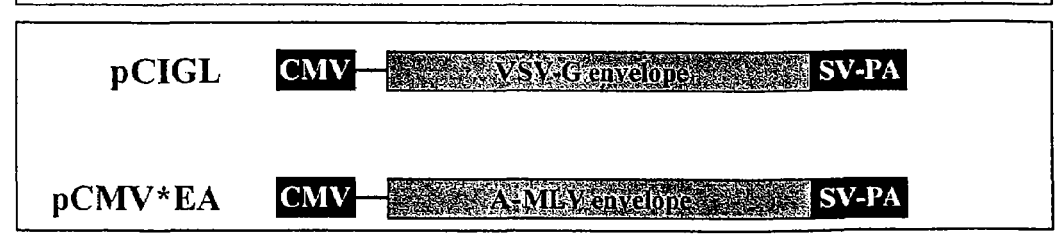

The practice of the present invention will employ, unless otherwise indicated, conventional techniques of cell biology, molecular biology, cell culture, virology, and the like which are in the skill of one in the art. These techniques are fully disclosed in current literature and reference in made specifically to Sambrook, Fritsch and Maniatis eds., "Molecular Cloning, A Laboratory Manual", 2nd Ed., Cold Spring Harbor Laboratory Press (1989); Celis J. E. "Cell Biology, A Laboratory Handbook" Academic Press, Inc. (1994) and Bahnson et al., J. of Virol. Methods, 54:131-143 (1995).

All publications and patent applications cited in this specification are indicative of the level of skill of those skilled in the art to which this invention pertains and are hereby incorporated by reference in their entirety.

The present invention is concerned with novel lentivirus-based packaging constructs that are useful for the establishment of stable packaging cell line and producer cell lines. Surprisingly it is found that mutations in the active site of the respective lentiviral protease gene enable the construction of lentiviral packaging vectors which are useful to establish stable packaging cell lines for the production of lentiviral vectors.

The catalytic center of HIV protease includes a three amino acid motif, Asp-Thr-Gly (Konvalinka, J. et al.,. J. Virol. 69:7180-7186,1995) These three amino acids are conserved among HIV and SIV isolates documented so far (Korber B, Theiler J, Wolinsky S Science 1998 Jun. 19 280: 5371 1868-71). Konvalinka, J. et al. mutated the Thr residue (corresponding to amino acid number 26 from the start of Protease in HIV isolate HXB2) to a Ser. They found that the mutated HIV protease has a significantly reduced toxicity while preserving the protease activity.

It has been surprisingly found that this information makes it possible for one to generate a stable cell line to express high levels of lentiviral Gag/Pol proteins. Expression of these proteins is absolutely necessary in order to establish a stable packaging cell line for lentiviral vectors, in particular for HIV- or BIV-based lentiviral vectors.

Furthermore, surprisingly, it was found in the present invention that the Asp-Thr-Gly motif is also present in BIV protease in the same location. A comparison of the first 29 Amino Acids of HIV and BIV proteases reveals that the amino acids number 25 to 29 are identical between HIV and BIV proteases, including the said Asp-Thr-Gly motif:

```
HIV Protease (HXB2):
1-PQVTLWQRPLVTIKIGGQLKEALLDTGAD      (SEQ ID NO:1)

BIV Protease (127 isolate):
1-SYIRLDKQPFIKVFIGGRWVKGLVDTGAD      (SEQ ID NO:2)

HIV Protease mut
1-PQVTLWQRPLVTIKIGGQLKEALLDSGAD      (SEQ ID NO:3)

BIV Protease mut
1-SYIRLDKQPFIKVFIGGRWVKGLVDSGAD      (SEQ ID NO:4)
```

Accordingly in one embodiment this invention provides for a mutation of the Thr to Ser in the BIV isolate 127 protease at the amino acid number 26 from the start of protease (SEQ ID NO:4) to generate a less toxic BIV protease as compared to wild type BIV protease. A BIV based stable packaging cell line, for BIV based lentiviral vector production, expressing BIV Gag/Pol with this point mutant in the protease coding region may then be generated. Such a stable packaging cell line allows for the development of a BIV lentiviral vector producing cell line.

In a further embodiment of the invention, it is found that combining the inclusion of protease genes having mutations in their active site with the inclusion of SAR elements into the lentiviral packaging construct may provide particularly advantageous results. Such packaging cell lines are capable of constitutively expressing particularly high levels of lentiviral proteins, such as for example the HIV p24 Gag protein. A high level of Gag (>5 ng/ml p24) is required for a stable packaging cell line to produce efficient titers. Preferably, the stable packaging cell line produces >100 ng/ml p24 and more preferably >1 μg/ml p24.

In one embodiment, the present invention provides a series of HIV-based packaging constructs. These packaging constructs are transfected into suitable cell lines (FIG. 1A). The original construct, pHIVΔΨ has been extensively used for transient production of vector supernatant, which has been very efficient at transducing a variety of target cells and tissues. The first modification introduced in order to make the packaging construct more suitable for stable vector production is the deletion of two accessory proteins, vif and vpr, to make pΔVΔR. Neither of these proteins is necessary for vector production (Zufferey et al, Nature Biotechnology. 15:871-875, 1997) and vpr has been shown to be cytostatic and might prevent the production of a stable producer cell line (Rogel, M. E. et al, J. Virol. 69:882-888, 1995). To further limit the potential toxicity of the construct, a point mutation is introduced into the active site of protease to produce pΔVΔR-PR*. This mutation has been reported to reduce the cytotoxicity caused by protease, but still allow normal viral processing functions (Konvalinka, J. et al.,. J. Virol. 69:7180-7186, 1995).

In a particular embodiment of this invention, a further modification to improve the stable expression of HIV Gag/Pol proteins is the introduction of the interferon β SAR element (Klehr, D et al.,. Biochemistry. 30:1264-1270, 1991). For example, such a modification results in the two vectors, pΔVΔR-SAR and pΔVΔR-PR*SAR.

The packaging constructs are tested for their ability to package an EGFP expressing vector and transduce 293T cells in the transient assay as described in the Examples below.

All of the vector supernatants that have been generated with the use of these constructs exhibit transduction efficiencies greater than 90% as measured by FACS analysis for EGFP expression indicating that the above-described modifications do not impair the normal packaging functions. Accordingly, it is found that stable packaging cell lines can be obtained if the packaging construct contains an active site mutation in the protease, which prevents toxicity and a SAR element. The SAR element may serve to reduce promoter silencing, although Applicants do not wish to be bound by any theoretical speculation as to the mechanistic explanation of the invention described.

Accordingly, in one aspect the present invention provides a lentiviral packaging construct comprising a deletion in the lentiviral packaging signal and a portion of the lentiviral pol gene which includes the protease encoding sequence, wherein said protease encoding sequence includes a mutation corresponding to a T26S substitution in the encoded lentiviral protease.

A lentiviral "packaging construct", also sometimes referred to as a helper construct, refers to an assembly which is capable of directing expression of one or more lentiviral nucleotide sequences that provide in trans the proteins required to obtain lentiviral vector particles. In one embodiment of the invention the nucleotide sequences include at least the gag gene and/or pol gene of a lentivirus; a promoter operably linked to the respective nucleotide sequences and generally a polyadenylation sequence located downstream of the respective nucleotide sequences encoding the gag and/or pol genes. The polyadenylation sequence, for example, may be derived from Simian virus 40 (SV40).

A mutation "corresponding to" a T26S substitution in the encoded lentiviral protease may be either the T26S substitution itself, which is the preferred substitution of the invention, or a substitution having an equivalent biologic effect. "Equivalent biologic effect" means a substitution resulting in a similar loss of protease cytotoxicity as the T26S substitution itself, while retaining a similar level of viral protease activity as the T26S substitution itself. Cytotoxicity may be measured as described in Konvalinka, J. et al.,. J. Virol. 69:7180-7186, 1995, in particular vimentin cleavage may be used as a marker for cytotoxicity. "Viral protease activity" may be measured as described in Konvalinka, J. et al.,. J. Virol. 69:7180-7186, 1995. In particular, cleavage of particle-associated polyproteins in the virus having the mutation to be assessed is a suitable measure for viral protease activity. Activities and cytotoxicities are "similar" within the meaning of the invention when the difference to those measured for the T26S substitution under essentially the same experimental conditions is less than 2 fold, preferably less than 1.5 fold or even less than 1.2 fold.

Generally, within the meaning of the invention, lentiviruses are exogenous, non-oncogenic retroviruses and include, but are not limited to, equine infectious anemia virus (EIAV; U.S. Pat. No. 6,277,633), simian immunodeficiency viruses (SIVs), visna and progressive pneumonia viruses of sheep, feline immunodeficiency virus (FIV), bovine immunodeficiency virus (BIV) and human immunodeficiency viruses (HIV-1 and HIV-2).

The lentiviral genome includes three genes found in retroviruses: gag, pol and env, which are flanked by two long terminal repeat (LTR) sequences. The gag gene encodes the internal structural proteins, such as matrix, capsid and nucleocapsid proteins; the pol gene encodes the RNA-directed DNA polymerase (reverse transcriptase (RT)), a protease and an integrase; and the env gene encodes viral envelope glycoproteins. The 5' and 3' LTR's serve to promote transcription and polyadenylation of the virion RNA's. The LTR contains all other cis-acting sequences necessary for viral replication. Lentiviruses may have additional genes including vif, vpr, tat, rev, vpu, nef and vpx (in HIV-1, HIV-2 and/or SIV). Adjacent to the 5' LTR are sequences necessary for reverse transcription of the genome, such as the tRNA primer binding site, and for efficient encapsidation of viral RNA into particles, such as the Psi site. If the sequences necessary for encapsidation are missing from the viral genome, such a cis defect will prevent encapsidation of genomic RNA. However, the resulting mutant remains capable of directing the synthesis of all virion proteins.

In one embodiment of the invention the packaging construct of the invention comprises a lentiviral gag gene. The gag gene is the 5'-most gene on retroviral genomes and, as has been described in more detail above, encodes structural proteins that are required to form the virus particle. The gag gene is translated to give a precursor polyprotein that is subsequently cleaved to yield three to five structural proteins. In a preferred embodiment, the gag gene is recoded.

A gene that is "recoded" refers to a gene or genes that are altered in such a manner that the polypeptide encoded by a nucleic acid remains the same as in the unaltered sequence but the nucleic acid sequence encoding the polypeptide is changed. It is well known in the art that due to degeneracy of the genetic code, there exist multiple DNA and RNA codons which can encode the same amino acid translation product. For example, in one embodiment, a DNA sequence encoding the gag and or pol genes of BIV is "recoded" so that the nucleotide sequence is altered but the amino acid translation sequence for the GAG and POL polypeptides remain identical to the wildtype amino acid sequence. Furthermore, it is also known that different organisms have different preferences for utilization of particular codons to synthesize an amino acid. Recoding can be accomplished using various techniques known in the art or modification thereof, for example, as taught in Casimiro D. R., Wright P. E., Dyson H. J., "PCR-based gene synthesis and protein NMR spectroscopy", Structure, 1997 Nov. 15, 5(11):1407-12; Brocca S., Schmidt-Dannert C., Lotti M., Alberghina L., Schmid R. D., "Design, total synthesis, and functional overexpression of the *Candida rugosa* lip1 gene coding for a major industrial lipase", Protein Sci., 1998 June, 7(6):1 415-22 Related Articles, Books, LinkOut Design; Withers-Martinez C., Carpenter E. P., Hackett F., Ely B., Sajid M., Grainger M., Blackman M. J., "PCR-based gene synthesis as an efficient approach for expression of the A+T-rich malaria genome", Protein Eng., 1999 December, 12(12):1113-20; Stemmer W. P., Crameri A., Ha K. D., Brennan T. M., Heyneker H. L., "Single-step assembly of a gene and entire plasmid from large numbers of oligodeoxyribonucleotides", Gene, 1995 Oct. 16, 164(1):49-53.

In one preferred embodiment of the present invention the packaging construct of the invention is derived from the HIV genome. In a particularly preferred embodiment the packaging construct further comprises a mutation in a HIV vif or vpr gene. Further particularly preferred embodiments of the present invention are the pΔVΔR-PR* construct and the pΔVΔR-PR*SAR construct as described in the Examples hereinbelow.

In one preferred embodiment the packaging construct is derived from the BIV genome. The basic genomic organization of BIV is disclosed in Garvey et al., (Virology, 175:391-409, 1990) and U.S. Pat. No. 5,380,830. Additionally disclosed are methods of obtaining BIV genomic DNA from BIV infected cells. Sequences encoding BIV and plasmids containing retroviral genomes suitable for use in preparing the vector constructs may be readily obtained given the disclosure provided herein or from depositories and databases such as the American Type Culture Collection (ATCC), for example, ATCC Accession No. 68092 and ATCC Accession No. 68093 and GENBANK. BIV based vectors are described in PCT Publication WO 01/44458.

The gag and pol genes are in different frames and overlap. The pol and env genes are in the same reading frame and are separated by the "central region". There are five open reading frames (ORFs) found in the central region. Three of these are similar in structure to the exons for vif, tat and rev of HIV and other lentiviruses. The other two ORFs are located in a position in the central region analogous to vpr, vpx and vpu encoding ORFs of HIV-1 and/or HIV-2. The nef ORF which is located post-env in the genomes of other lentiviruses appears to be lacking in BIV.

It will be understood that for the nucleotide sequence of the BIV genome, natural variations can exist between individual BIV viruses. These variations may result in deletions, substitutions, insertions, inversions or additions of one or more nucleotides as long as the claimed function of the gene is not lost. The DNA sequences encoding such variants may be created by standard cloning methods or polymerase chain reaction (PC R), see U.S. Pat. Nos. 4,683,195 and 4,683,202. The present invention relates to a nucleic acid segment from a BIV genome obtainable from any strain or clone of BIV. In one embodiment of this invention, the BIV vector construct of the invention includes a sufficient number of nucleotides corresponding to nucleotides of the BIV genome to express one or more functional BIV genes.

In a preferred embodiment the BIV-derived packaging construct of the invention may comprise a mutation in, including deletion of all or a portion of, a BIV vif, W, Y or tat gene. The BIV Rev gene and Rev-responsive element (RRE) may also be mutated or deleted if Constitutive Transport Element (CTE) is used in the BIV vector of the invention.

In a further embodiment of the invention, the lentiviral vector of the present invention comprises a DNA scaffold attachment region (SAR), which as broadly defined herein, refers to a DNA sequence having an affinity or intrinsic binding ability for the nuclear scaffold or matrix. Particularly preferred is an IFN-SAR element and most preferred is a β-IFN-SAR element. SAR elements are usually 100 to 300 or more base pairs long, and may require a redundancy of sequence information and contain multiple sites of protein-DNA interaction. SAR elements are DNA elements which bind to the isolated nuclear scaffold or matrix with high affinity (Cockerill, P. N. and Garrard, W. T. (1986). Cell 44: 273-282, Gasser, S. M. and Laemmli, U. K. (1986). Cell 46: 521-530). Some of the SAR sequences have been shown to have enhancer activities (Phi-Van, L., et al (1990). Mol. Cell Biol. 10: 2302-2307, McKnight, R. A., et al. (1992). Proc. Natl. Acad. Sci. USA 89: 6943-6947), and some serve as cis-acting elements, driving B-cell specific demethylation in the immunoglobulin k locus (Lichtenstein, M. et al., (1994). Cell 76: 913-923, Kirillov, A. et al., (1996). Nat. Genet. 13: 435-441). The hIFN-β SAR element inhibits de novo methylation of the 5' LTR, and appears to insulate the transgene from the influence of the flanking host chromatin at the site of retroviral integration. Position effects are thus decreased. SAR elements may be obtained, for example, from eukaryotes including mammals, plants, insects and yeast, preferably mammals. Examples of suitable protocols for identifying SAR elements for use in the present invention are described in WO96/19573.

Preferably the SAR elements should be located downstream from the transgene and the lentiviral env sequence. In one embodiment, more than one SAR element may be inserted into the packaging vector of the invention. Although Applicants do not wish to be bound by mechanistic speculation, the use of flanking SAR elements in the nucleic acid molecules may allow the SAR elements to form an independent loop or chromatin domain, which is insulated from the effects of neighboring chromatin.

Other methods may be used in addition or as an alternative to using SAR elements. These methods include integrating the gag/pol expression construct in a highly expressed region of a chromosome or a highly expressed gene. These highly expressed regions include, but are not limited to, SARs, locus control regions (LCRs), and insulator regions (Emery, et al., PNAS, 97(16):9150-9155 (2000)). It will be evident to one skilled in the art that there are several methods which can be employed to integrate a gag/pol expression construct into a highly expressed region or gene (e.g., homologous recombination).

In a further aspect of the present invention there is provided a stable pre-packaging cell line comprising the packaging construct of the invention. Particularly preferred pre-packaging cell lines are such cell lines which are capable of stably expressing at least 5 ng/ml of the HIV p24 protein, or at least 5 ng/ml of BIV reverse transcriptase (RT) protein, and wherein such protein expression is constitutive. Preferably, 50 ng/ml of BIV RT is produced. More preferably, 500 ng/ml BIV RT is produced.

In a further aspect of the present invention there is provided a stable packaging cell line comprising the packaging construct of the invention and further comprising a plasmid comprising an env gene. Accordingly, a "packaging cell line" within the meaning of the invention is a recombinant cell line containing nucleic acid sequences expressing retroviral Gag, Pol and Env structural proteins. Because the packaging cell line lacks the retroviral nucleic acid sequence of the packaging signal and other cis-acting elements, infectious virions cannot be produced.

The "env" gene encodes the envelope proteins. As used in this disclosure, the env gene includes not only natural env gene sequences but also modifications to the env gene including modifications that alter target specificity of retroviruses and lentiviruses or env genes that are used to generate pseudotyped retrovirus/lentivirus, reference is made to PCT Publications WO 92/14829, WO 94/11524, and U.S. Pat. No. 6,004,798. The env gene can be derived from any virus, including retroviruses. The env preferably is an amphotropic envelope protein which allows transduction of cells of human and other species. It may be desirable to target the recombinant virus by linkage of the envelope protein with an antibody or a particular ligand for targeting to a receptor of a particular cell-type. By inserting a sequence including a regulatory region of interest into the viral vector, along with a gene which encodes the ligand for a receptor on a specific target cell the vector may be rendered target-specific. For example, vectors can be made target-specific by inserting, for example, a glycolipid or a protein. Further, targeting may be accomplished by using an antigen-binding portion of an antibody or a recombinant antibody-type molecule, such as a single chain antibody, to target the retroviral vector. The person skilled in the art will know of, or can readily ascertain without undue experimentation, specific methods to achieve delivery of a retroviral vector to a specific target.

Generally, the cell lines of the invention may include separate vectors which provide the packaging functions of recombinant virions, such as, gag, pol, env, tat and rev, as discussed above. There is no limitation on the number of vectors which are utilized so long as the vectors are used to transform and to produce the packaging cell line to yield recombinant lentivirus. The vectors are introduced via transfection or infection into the packaging cell line. The packaging cell line produces viral particles that contain the vector genome. Methods for transfection or infection are well known by those of skill in the art. After cotransfection of the packaging vectors and the transfer vector to the packaging cell line, the recombinant virus is recovered from the culture media and titered by standard methods used by those of skill in the art. Thus, the packaging constructs can be introduced into human cell lines for example by calcium phosphate transfection, lipofection or electroporation, generally together with a dominant selectable marker, such as neo, DHFR, Gln synthetase or ADA, followed by selection in the presence of the appropriate drug and isolation of clones.

In a preferred embodiment the packaging cell line of the invention includes the VSV-G env gene. While VSV-G protein is a desirable env gene because VSV-G confers broad host range on the recombinant virus, VSV-G can be deleterious to the host cell. Thus, when a gene such as that for VSV-G is used, it is preferred to employ an inducible promoter system so that VSV-G expression can be regulated to minimize host toxicity when VSV-G expression is not required. For example, the tetracycline-regulatable gene expression system of Gossen & Bujard (Proc. Natl. Acad. Sci. (1992) 89:5547-5551) can be employed to provide for inducible expression of VSV-G. The tet/VP16 transactivator may be present on a first vector and the VSV-G coding sequence may be cloned downstream from a promoter controlled by tet operator sequences on another vector. Other non-limiting examples of regulatable expression systems are described in PCT Publications WO 01/30843 and WO 02/06463.

In another preferred embodiment, the packaging cell line of the invention includes the LCMV mutant env gene (Beyer, et al., J. Virol., 76:1488-1495). In one embodiment, the LCMV mutant env gene is constitutively expressed. In another embodiment, the LCMV mutant env gene is expressed from an inducible promoter. Inducible promoter systems are described hereinabove.

In a further aspect of the present invention there is provided a producer cell line comprising the packaging construct of the invention, an env gene and further comprising a lentiviral vector, i.e. a vector comprising a lentiviral 5'LTR, a lentiviral 3'LTR and a suitable packaging signal. Accordingly, a "producer cell line" is a packaging cell line as defined above which also contains a replication-defective lentiviral vector which is packaged into the vector particle. The producer cell produces lentiviral-based particles, which may contain "heterologous" (i.e., non-lentiviral) genes, such as therapeutic or marker genes.

In a preferred embodiment the producer cell line of the invention is further characterized in that it is capable of producing a lentiviral virus titer of at least 10E5 cfu/ml and preferably ≧10 E6 cfu/ml.

In yet another aspect a lentiviral vector particle obtained from the stable producer cell line of the invention is provided. Also provided is a method for producing a lentiviral vector particle preparation comprising the steps of transfecting the stable packaging cell line of the invention with a lentiviral vector, isolating and propagating a producer cell line in a suitable culture medium and obtaining a lentiviral vector particle preparation from the said culture medium.

Generally, viral supernatants are harvested using standard techniques such as filtration of supernatants at an appropriate time-point, such as for example 48 hours after transfection. The viral titer is determined by infection of suitable cells with an appropriate amount of viral supernatant. For example, forty-eight hours later, the transduction efficiency is assayed. Thus, the instant invention provides methods and means for producing high titer recombinant lentiviral vector particles. Such particle preparations can subsequently be used to infect target cells using techniques known in the art.

The following examples are provided for the purpose of further illustrating the present invention but are in no way to be taken as limiting.

EXAMPLES

Example 1

HIV-Based Packaging Vector Construction

The packaging plasmids used in this study are depicted in FIG. 1A. pHIVΔΨ contains the sequence of the HIV-1 NL4-3 isolate with deletions of 1) both LTRs, 2) 33 bp of the packaging signal (Ψ) 5' to the gag gene, 3) 1587 bp of the env gene, 4) the vpu gene and 5) the nef gene. All the other genes are unaffected. Transcription of the HIV genes is under the control of the Cytomegalovirus (CMV) promoter, derived from the pCI vector (Promega, Wis.). pHIVΔΨ is a modification of pHIV-PV (Sutton, R. E., H. T. M. Wu, R. Rigg, E. Bohnlein, and P. O. Brown. 1998. 72:5781-5788). A 660 bp NdeI/SalI fragment was deleted from pHIVΔΨ to remove vif and vpr, resulting in pΔVΔR. A point mutation (nt 2328, A to T)) was introduced into the protease gene of pΔVΔR using PCR mutagenesis to make pΔVΔR-PR*. This corresponds to an amino acid substitution of Thr26 to Ser26. The PCR primers for the mutagenesis are as follows:

```
Primer A:
5'-AATTGCAGGGCCCCTAGGAAAAA-3'      (SEQ ID NO:5)

Primer B:
5'-TCTGCTCCTGA ATCTAATAGCGCTT-3'   (SEQ ID NO:6)
```

```
-continued
Primer C:
5'-AAGCGCTATTAGATTCAGGAGCAGA-3'    (SEQ ID NO:7)

Primer D:
CCATGTACCGGTTCTTTTAGAATC-3'.       (SEQ ID NO:8)
```

Primers B and C are complementary and contain the A to T mutation (nt 2328), which confers the Thr to Ser amino acid substitution and a T to G mutation (nt 2318), which introduces a unique Eco47III restriction site, but does not alter the amino acid sequence. The PCR product amplified from primers A & B was purified and combined with the purified product amplified from primers C & D. This mix was then amplified with primers A & D, cut with ApaI and AgeI (restriction sites naturally present in the primers) and then cloned back into pΔVΔR. The presence of the mutation was confirmed by Eco47II digestion and sequence analysis. The interferon β scaffold attachment region (SAR) (800 bp fragment) (Agarwal, M., T. W. Austin, F. Morel, J. Chen, E. Böhnlein, and I. Plavec. 1998. 72:3720-3728) was introduced into a NotI restriction site (nt 8800) for both pΔVΔR and pΔVΔR-PR* to create pΔVΔR-SAR and pΔVΔR-PR*SAR, respectively. The transfer vector used in these studies, pHLEIP, is shown in FIG. 1B. pHLEIP contains sequences from the HIV-1 NL4-3 isolate including 1) both LTRs, 2) 1251 bp of the 5' end of gag, 3) 715 bp of the 3' end of pol, which contains the central polypurine tract (ppt) and transcriptional enhancer sequences, 4) 311 bp encoding the first exons of tat and rev, and 5) 977 bp of env containing the REV response element (RRE) and the second exon of tat. The nef and rev coding sequences are disrupted by the insertion of the egfp marker gene (Clontech, CA.), followed by the picornoviral internal ribosomal entry site (Jang, S. K., M. V. Davies, R. J. Kaufman, and E. Wimmer. 1989. J. Virol. 63:1651-1660) and the puromycin N-acetyltransferase gene (Vara, J. A., A. Portela, J. Ortin, and A. Jimenez. 1986. Nuc. Acids Res. 14:4617-4624). The expression of egfp is controlled by the HIV LTR in a tat-dependent manner. This vector is a modification of pHIV-AP G⁻P⁻E⁻F⁻V (Sutton, R. E., H. T. M. Wu, R. Rigg, E. Bohnlein, and P. O. Brown. 1998. Journal of Virology. 72:5781-5788). The envelope constructs used for pseudotyping are pCIGL, which contains the VSV-G gene (Burns, J. C., T. Friedmann, W. Driever, M. Burrascano, and J.-K. Yee. 1993. Proceedings of the National Academy of Sciences, USA. 90:8033-8037; Yee, J. K., A. Miyanohara, P. LaPorte, K. Bouic, J. C. Burns, and T. Friedmann. 1994. Proceedings of the National Academy of Sciences USA. 91:9564-9568) under the control of the CMV promoter from pCI, and pCMV*Ea, which contains the amphotropic murine leukemia virus (A-MLV) envelope gene cloned into pCI (Rigg, R. J., J. Chen, J. S. Dando, S. P. Forestell, I. Plavec, and E. Bohnlein. 1996. Virology. 218:290-295) (FIG. 1C).

Example 2

Functional Analysis of Packaging Constructs

A transient assay was performed to verify that the packaging constructs retained all necessary functions. First viral supernatants were generated by transfecting 293T cells ($5 \times 10^6$) with 3 constructs (10 μg packaging construct, 5 μg envelope construct, and 20 μg transfer vector), by $Ca_2PO_4$ precipitation (Clontech, CA.). The transfection supernatants were collected after 24, 48 and 72 hours, pooled and filtered through a 0.45 μm filter. To determine transduction efficiencies, the collected vector supernatants were diluted 1:1 with culture medium (DMEM plus 10% FBS), added to 2×10⁵ 293T cells plated on a 6 well dish, and centrifuged at 2500×g in the presence of 8 µg/ml protamine sulfate (Sigma, MO.). This transduction protocol known as "spinoculation" (Bahnson, A. B., J. T. Dunigan, B. E. Baysal, T. Mohney, R. W. Atchison, M. T. Nimgaonkar, E. D. Ball, and J. A. Barranger. 1995, J Virol Meth. 54:131-143) was performed at 37° C. for 3-4 hours. After spinoculation, the medium was replaced and the cells were cultured at 37° C. for 48-72 hr. After incubation, the cells were fixed in 1-2% formaldehyde and EGFP expression was measured by flow cytometry on a FACScan (Becton Dickinson, MD.).

Example 3

Production of Producer Cell Lines

To generate Gag/Pol producer cell lines, 293 Ea6 cells (5×10⁶) were plated in a 10 cm dish and transfected with 2 constructs (10 µg packaging construct and 1 µg pcDNApuro) by Ca$_2$PO$_4$ precipitation (Clontech, CA.). PCDNApuro is a plasmid containing the puromycin N-acetyltransferase gene driven by the CMV promoter from pCDNA1.1/Amp (Invitrogen, CA.). The 293 Ea6 cell line constitutively expresses the A-MLV envelope (Rigg, R. J., J. Chen, J. S. Dando, S. P. Forestell, I. Plavec, and E. Bohnlein. 1996. Virology. 218: 290-295). After transfection, the cells were cultured for 48 hrs and then transferred to medium containing 5 µg/ml puromycin (Sigma, MO.). The cells were maintained under puromycin selection and monitored periodically for Gag production via p24 ELISA (Beckman/Coulter, CA.). To measure p24 production of the cell line, 1×10⁶ cells were plated in a well of a 6-well dish, supernatant was collected 24 hr post plating, filtered through a 0.45 µn filter, and then assayed by p24 ELISA. Single cell clones were obtained from the cell line expressing the highest level of p24 by sorting on a FACStar (Becton Dickinson, MD.). The transfer vector, pHLEIP was introduced into the clone with the highest stable production of p24. This was achieved by transducing the clone with transient VSV-G pseudotyped pHLEIP vector supernatant as described in the previous section. Supernatants from the resulting packaging line were collected at various times post transduction and titered on 293T cells. For titering, 2×10⁵ 293T cells were plated in wells of a 6-well dish and transduced as previously described with 10 fold serial dilutions of viral supernatant. After 48 hr of culture, 5 µg/ml puromycin was added to the medium for selection. The cells were then maintained in selection medium for 2 weeks. The surviving colonies were fixed and stained in coomassie blue solution (50% methanol, 0.05% coomassie brilliant blue R-250, 10% acetic acid) and counted to determine the titer.

Example 4

Evaluation of Packaging Constructs for Stable p24 Production

Figure 2:
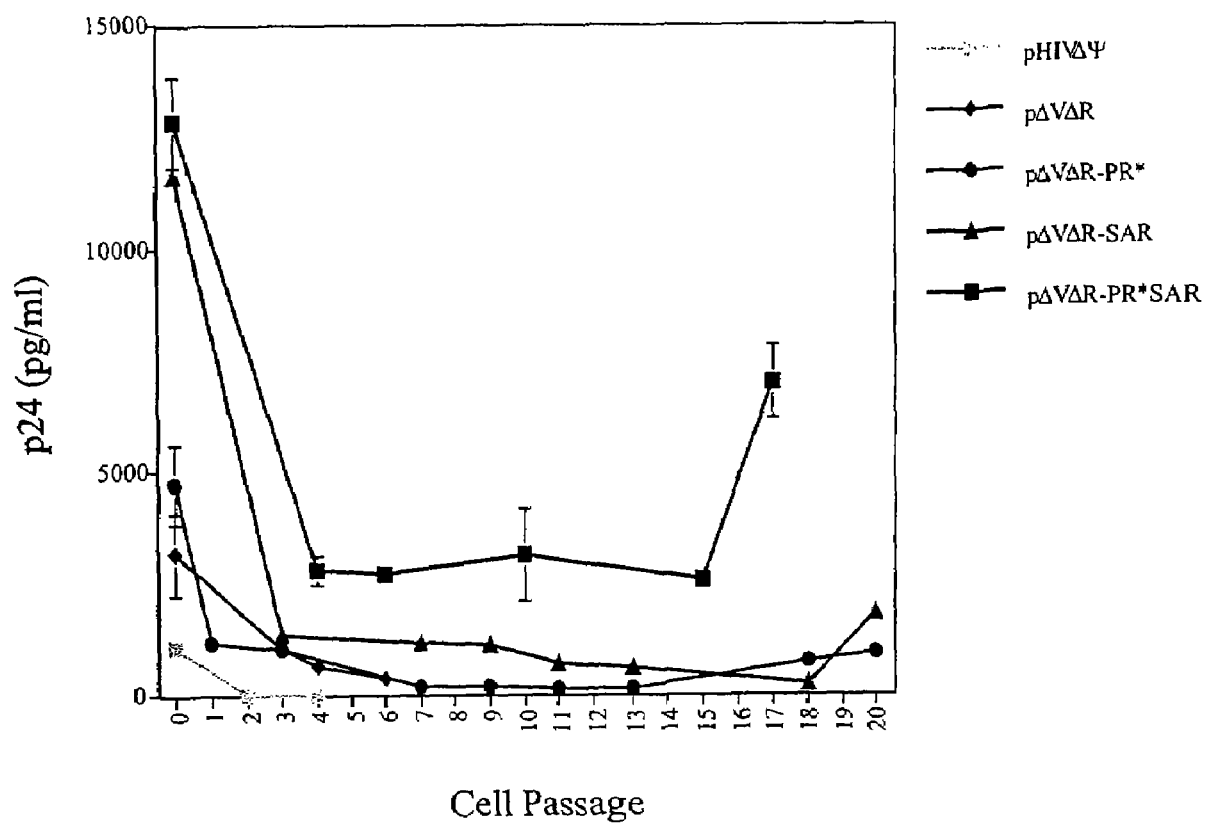
FIG. 2 is a graph comparing the viral production, as measured by HIV p24 levels, from the different HIV packaging cell lines over time (approximately 12 weeks).

To determine if any of the modified packaging constructs could confer long-term, high-level Gag/Pol protein expression, stable 293 Ea6-based cell lines were generated and monitored for viral particle production at regular intervals after selection as described in Materials and Methods. FIG. 2 is a graph comparing the viral production, as measured by p24 levels, from the different packaging cell lines over time (approximately 12 weeks). As expected, the cells containing the construct with vpr, pHIVΔΨ, expressed low levels of p24 soon after selection and by the second passage the p24 expression was below the level of detection. The cell line made with the vpr-deleted construct, pΔVΔR and the two cell lines containing either the protease mutation, pΔVΔR-PR* or the SAR insertion, pΔVΔR-SAR had higher initial p24 levels (3-12 ng/ml), but decreased to levels less than 1 ng/ml. Interestingly, the cell line containing the construct with both the protease mutation and the SAR insertion, pΔVΔR-PR*SAR, maintained about 4 times more p24 expression than the cells containing the single modification constructs. These results suggest that inhibiting both protease toxicity and promoter silencing can increase the levels and stability of p24 expression in a cell line, but that either modification alone provides no significant improvement.

Example 5

Clonal Analysis of Modified Packaging Constructs

Although the cell line containing the double modified construct, pΔVΔR-PR*SAR expressed the highest levels of p24 compared to the other constructs, these levels are not sufficient to generate an efficient packaging cell line. Single cell clones were isolated from this cell line in an attempt to find a high p24 producing clone. As shown in Table 1 the majority of clones expressed negligible levels of p24, but 2 of the 40 clones analyzed expressed significantly higher levels of p24 than the parent cell line (10-100 ng/ml). One of these clones (PR*SAR clone) expressed 100 ng/ml p24 for at least 12 weeks. To verify the importance of the protease mutation for allowing high-level p24 production, single cell clones were also obtained from the cell line containing pΔVΔR-SAR and analyzed for p24 production. Table 1 illustrates the comparison between clones containing the packaging constructs+/- the protease mutation. No pΔVΔR-SAR containing clones expressed p24 levels >10 ng/ml even though almost twice as many clones were evaluated compared to those containing pΔVΔR-PR*SAR. These results confirm the importance of the protease mutation in producing high-level Gag/Pol producer cells.

TABLE 1

Clonal analysis confirms the importance of the protease mutation in obtaining a high-level Gag producing cell line

| | p24 Production (ng/ml) | | | |
|---|---|---|---|---|
| Cell line | Background Level* | 1-10 | 10-100 | Total # of clones |
| ΔVΔR-PR*SAR | 33 | 5 | 2 | 40 |
| ΔVΔR-SAR | 71 | 5 | 0 | 76 |

*Background Level is <20 pg/ml p24

Example 6

Titer of Highest Gag/Pol-Producing Packaging Cell Clone

To determine how efficiently the PR*SAR clone could package and transfer vector, a titration analysis was performed. A transiently produced VSV-G pseudotyped vector containing EGFP and a puromycin resistance gene, pHLEIP was introduced into the packaging cell clone via transduction, as described in Materials and Methods. Supernatants were collected at various time points post transduction, analyzed for p24 production, and titered on 293T cells via EGFP FACS and puromycin selection. As shown in Table 2 Expt. 1, the p24 production at the 24 hr time point was 91 ng/ml and the titers of supernatant collected at both 24 and 48 hours were $5 \times 10^4$ IU/ml as determined by puromycin selection. Expt. 2 was similar to expt. 1 except the virus was allowed to accumulate over the indicated collection times before analysis. Under these conditions, the p24 production went from 954 ng/ml at 48 hr to 2300 ng/ml by 96 hr. These levels are now in the range produced by the transient system (1-10 μg/ml) (data not shown). Interestingly, although the p24 levels increased with accumulation, the supernatants from all three time-points had similar titers ($4-6 \times 10^4$ IU/ml) on 293T cells. This corresponded to <1% EGFP expression in 293T cells transduced with the 48 hr and 72 hr accumulated supernatants. Also, while the viral supernatants generated from the transient system have p24 levels corn parable to the PR*SAR clone after accumulation, they routinely have titers of $5-10 \times 10^6$ IU/ml (Table 3). This data suggests that p24 production is probably not the limiting factor in achieving high titers from the packaging clone.

TABLE 2 p24 production and titer of PR*SAR clone

| Experiment | Supernatant Collection | p24 Production (ng/ml) | Titer IU/ml (Puromycin Selection) | % EGFP (FACS) |
|---|---|---|---|---|
| Expt. 1 | 24 hr | 91 | $5 \times 10^4$ | ND |
|  | 48 hr | ND | $5 \times 10^4$ | ND |
| Expt. 2 | 48 hr accumulation | 954 | $4-6 \times 10^4$ | 0.90 |
|  | 72 hr accumulation | 1800 | $4-6 \times 10^4$ | 0.80 |
|  | 96 hr accumulation | 2300 | $4-6 \times 10^4$ | ND |

Example 7

Effect of Envelope Expression on Titer of Packaging Cell Clone

To determine if a loss of envelope expression could be contributing to the lower titers of the PR*SAR packaging clone, first a FACS analysis was performed to verify A-MLV env expression. An equivalent level of envelope was detectable by FACS compared to the 293 Ea6 parent cell line. To further test whether the envelope was limiting, envelope-expressing constructs were transfected into the PR*SAR packaging clone, which had already been stably transduced with the pHLEIP vector. Both VSV-G and A-MLV env expression constructs were used. Table 3 shows a comparison of the titers and transduction efficiencies of supernatant from the stable packaging clone in the presence or absence of additional envelope. The addition of VSV-G increased the titer 5-8 fold and allowed for a detectable transduction efficiency of 14%. The addition of A-MLV env also increased the titer, but only 2 fold. These results indicate that the titer of the PR*SAR packaging cell clone can be improved by increasing envelope expression.

The levels of Gag produced from our PR*SAR packaging clone, reach the levels obtained with the transient packaging system. However, the titers are still lower than with the transient system. We have shown that envelope is limiting in the clone we isolated, therefore screening more clones based on envelope expression as well has p24 production might increase the probability of obtaining a higher titer clone. In addition, the transfer vector was introduced into the packaging clone by only one round of transduction, thereby limiting the vector copy number. Increasing the vector copies in the packaging cell line should also improve titers.

TABLE 3

The titer and transduction efficiency of the PR*SAR clone is improved with increased envelope expression

| Packaging System | Added Envelope | Titer IU/ml (Puromycin Selection) | % EGFP (FACS) |
|---|---|---|---|
| Stable | None | $4-6 \times 10^4$ | <1 |
|  | A-MLV | $1 \times 10^5$ | ND |
|  | VSV-G | $3 \times 10^5$ | 14 |
| Transient | A-MLV | $5 \times 10^6$ | 22 |
|  | VSV-G | $2 \times 10^7$ | 91 |

Example 8

Construction of Packaging Constructs for BIV Based Lentiviral Vectors

To generate a BIV based lentiviral packaging construct, CTE is P CR amplified with two primers CTE1 (5'-CGGGG-TACCACCTCCCCTGTGAGCTAG-3') (SEQ ID NO:9) and CTE2 (TGCTCTAGAGACACATCCCTCGGAGGC-3') (SEQ ID NO:10). The amplified product is digested with KpnI and XbaI and ligated to a pCI plasmid previously digested with KpnI and XbaI, generating pCI.CTE. Second, BIV gag and pol coding sequence is PCR amplified with two primers GAG5 (5'-CCGCTCGAGATGAAGAGAAGGC-GAGTTAGAA-3') (SEQ ID NO:11) and POL3 (5'-CCGCTCGAGTCACGAACTCCCATCTTGGAT-3') (SEQ ID NO:12). The amplified product is digested with XhoI and ligated to pCI.CTE previously digested with XhoI, generating a BIV based packaging construct, pCIBIVGP. Alternatively, CTE can be replaced by BIV RRE (Rev-responsive element) and Rev. To create the Threonine to Serine in BIV protease (corresponding to amino acid number 26 from the start of pProtease) to generate a potentially less toxic BIV protease, pCIBIVGP is subjected to PCR amplification with primer Primer A (5'-GGGTTAGTAGACTCTGGA-3') (SEQ ID NO:13) and Primer B (5'-GCCCGGGTCGACTCTAGA-3') (SEQ ID NO:14). Primer B contains the A to T mutation, which confers the Thr to Ser amino acid substitution. The PCR product amplified from primers A and B is digested with AccI and ligated to pCIBIVGP previously digested with AccI resulting in pCIBIVGPmut with the desired mutation in the protease.

Example 9

Figure 3:
FIG. 3 shows schematic of pCligpSyn.

BIV Packaging Constructs with Recoded gag/pol Sequence or Recoded gag/pol Sequence with Specific Mutation in Protease Without being bound by theory, lentiviruses such as HIV, SIV and BIV are thought to contain nucleic acid sequences in their viral RNAs which cause RNA instability, thereby preventing efficient nuclear export of viral RNAs. This is believed to be due to the fact that lentiviruses employ rare codon usage and/or RNA secondary structure which is determined by the RNA sequence. The viral RNAs containing these rare codons can not be efficiently transported out of the nucleus without Rev/RRE. We recoded the BIV gag/pol coding sequence using preferred *Homo sapiens* codons (Table 4)

to eliminate RRE from the packaging construct, to minimize or eliminate the overlaps between the packaging and transfer vector constructs and to increase the BIV gag/pol gene expression levels. The sequence as in SEQ ID NO:15 was selected for the recoded gag/pol construct. The company Aptagen (Herdon, VA.) was contracted to clone this DNA construct. The recoded gag/pol coding sequence was cloned into the pCI mammalian expression vector, generating pCligpSyn (FIG. 3). The generation of pCligpSyn allowed us to produce BIV vectors from a four component system by cotransfecting pCligpSyn, pTracerARev (a BIV Rev expression construct containing SEQ ID NO:16; Table 7), pBIVminivec (a BIV-based transfer vector construct encoding GFP), and pCMVVSV-G (a VSV-G expression construct). The BIV vectors generated from this system with recoded gag/pol were fully functional as indicated by their ability to efficiently transduce cells (Table 5).

TABLE 4

Sequence of recoded gag/pol (SEQ ID NO:15)

ATGAAGCGGAGAGAGCTGGAGAAGAAACTGAGGAAAGTGCGCGTGACACC

TCAACAGGACAAGTACTATACCATCGGCAACCTGCAGTGGGCCATCCGCA

TGATCAACCTGATGGGCATCAAGTGCGTGTGCGACGAGGAATGCAGCGCC

GCTGAGGTCGCCCTGATCATCACCCAGTTTAGCGCGCTCGACCTGGAGAA

CTCCCCTATCCGCGGCAAGGAAGAGGTGGCCATCAAGAATACCCTGAAGG

TGTTTTGGAGCCTGCTGGCCGGATACAAGCCTGAGAGCACCGAGACCGCC

CTGGGATACTGGGAAGCCTTCACCTACAGAGAGAGGGAAGCTAGAGCCGA

CAAGGAGGGAGAGATCAAGAGCATCTACCCTAGCCTGACCCAGAACACCC

AGAACAAGAAACAGACCAGCAATCAGACAAACACCCAGAGCCTGCCCGCT

ATCACCACACAGGATGGCACCCCTCGCTTCGACCCCGACCTGATGAAGCA

GCTGAAGATCTGGTCCGATGCCACAGAGCGCAATGGAGTGGACCTGCATG

CCGTGAACATCCTGGGAGTGATCACAGCCAACCTGGTGCAAGAAGAGATC

AAGCTCCTGCTGAATAGCACACCCAAGTGGCGCCTGGACGTGCAGCTGAT

CGAGAGCATAAGTGAGAGAGAAGGAGAACGCCCACCGCACCTGGAAGCAG

CATCACCCTGAGGCTCGCAAGACAGACGAGATCATTGGAAAGGGACTGAG

CTCCGCCGAGCAGGCTACCCTGATCAGCGTGGAGTGCAGAGAGACCTTCC

GCCAGTGGGTGCTGCAGGCTGCCATGGAGGTCGCCCAGGCTAAGCACGCC

ACACCCGGACCTATCAACATCCATCAAGGCCCTAAGGAACCCTACACCGA

CTTCATCAACCGCCTGGTGGCTGCCCTGGTAAGGAATGGCCGCTCCCGAG

ACCACAAAGGAGTACCTCCTGCAGCACCTGAGCATCGACCACGCCAACGA

GGACTGTCAGTCCATCCTGCGCCCTCTGGGACCCAACACACCTATGGAGA

AGAAACTGGAGGCCTGTCGCGTGGTGGGAAGCCAGAAGAGCAAGATGCAG

TTCCTGGTGGCCGCTATGAAGGAAATGGGGATCCAGTCTCCTATTCCAGC

CGTGCTGCCTCACACACCCGAAGCCTACGCCTCCCAAACCTCAGGGCCCG

AGGATGGTAGGAGATGTTACGGATGTGGGAAGACAGGACATTTGAAGAGG

AATTGTAAACAGCAAAAATGCTACCATTGTGGCAAACCTGGCCACCAAGC

AAGAAACTGCAGGTCAAAAAACGGGAAGTGCTCCTCTGCCCCTTATGGGC

AGAGGAGCCTAACCACAGAACAATTTTCACCAGAGCAACATGAGTTCTGT

TABLE 4-continued

Sequence of recoded gag/pol (SEQ ID NO:15)

GACCCCATCTGCACCCCCTCTTATATTAGATTAGACAAACAGCCTTTTAT

AAAGGTGTTCATTGGCGGCCGCTGGGTGAAGGGACTGGTGGACACAGGCG

CTGACGAGGTGGTGCTGAAGAACATCCACTGGGACCGCATCAAAGGCTAC

CCTGGAACACCCATCAAGCAGATCGGCGTGAACGGCGTGAACGTGGCTAA

GCGCAAAACACATGTGGAGTGGAGATTCAAAGACAAGACCGGCATCATTG

ACGTCCTCTTCAGCGACACACCTGTGAACCTGTTTGGCAGAAGCCTGCTC

AGATCCATCGTGACCTGCTTTACCCTGCTGGTGCACACCGAGAAGATCGA

GCCACTGCCTGTGAAGGTGCGCGGCCCTGGACCTAAGGTGCCACAATGGC

CCCTGACCAAGGAGAAATACCAGGCCCTGAAGGAGATCGTGAAGGACCTG

CTGGCCGAGGGAAAGATCAGCGAAGCTGCCTGGGACAACCCTTACAACAC

ACCCGTGTTCGTGATCAAGAAGAAAGGCACCGGCCGCTGGCGCATGCTGA

TGGACTTCCGCGAGCTGAATAAGATCACCGTGAAAGGCCAAGAGTTCAGC

ACAGGACTCCCTTATCCACCCGGCATCAAGGAGTGTGAGCACCTGACCGC

CATCGACATCAAGGACGCCTACTTCACCATCCCTCTGCACGAGGACTTCA

GACCCTTCACAGCCTTCAGCGTGGTCCCAGTGAACCGCGAGGGCCCCATC

GAGCGCTTCCAGTGGAACGTCCTGCCTCAAGGCTCAAGGTGTGCTCCCCT

GCCATCTACCAGACCACAACCCAGAAGATCATTGAGAACATCAAGAAGAG

CCATCCCGACGTGATGCTGTATCAGTACATGGATGACCTCCTGATTGGCA

GCAATCGCGATGACCACAAGCAGATCGTGCAGGAGATCAGAGACAAGCTG

GGCAGCTATGGCTTCAAGACACCCGACGAGAAAGTGCAGGAAGAGCGCGT

GAAGTGGATCGGCTTCGAGCTGACACCTAAGAAATGGAGATTCCAGCGTA

GGCAACTGAAGATCAAGAACCCACTGACCGTGAACGAACTCCAGCAGCTG

GTCGGCAACTGTGTGTGGGTGCAGCCCGAGGTGAAGATCCCTCTGTACCC

ACTGACCGATCTGCTCCGCGACAAGACCAACCTGCAGGAAAAGATCCAGC

TGACACCCGAGGCCATCAAGTGCGTGGAAGAGTTCAACCTGAAGCTGAAA

GATCCCGAGTGGAAGGACAGAATTCGCGAAGGAGCCGAGCTGGTGATCAA

GATCCAAATGGTCCCTCGCGGCATCGTGTTCGACCTGCTGCAAGACGGCA

ATCCTATCTGGGGAGGCGTGAAAGGACTGAACTACGACCACAGCAACAAG

ATCAAGAAGATCCTGCGCACCATGAACGAGCTGAACCGCACCGTGGTGAT

CATGACCGGACGCGAAGCTAGCTTTCTCCTGCCTGGATCCAGCGAGGATT

GGGAGGCCGCCCTGCAGAAGGAGAGAGCCTGACCCAAATCTTTCCCGTGA

AGTTCTACCGCCATAGCTGTAGATGGACAAGCATCTGTGGACCCGTCCGC

GAGAACCTGACCACCTACTATACCGACGGCGGGAAGAAAGGAAAGACAGC

TGCCGCAGTGTACTGGTGTGAAGGAAGAACTAAGAGCAAAGTGTTCCCTG

GAACCAATCAACAGGCTGAGCTGAAGGCAATCTGCATGGCTCTGCTGGAC

GGACCTCCCAAGATGAACATCATCACCGACAGCCGCTACGCTTATGAGGG

CATGAGAGAGGAACCTGAGACCTGGGCTCGCGAGGGCATCTGGCTGGAGA

TTGCAAAGATCCTGCCATTCAAGCAATACGTCGGAGTGGGCTGGGTCCCT

TABLE 4-continued

Sequence of recoded gag/pol (SEQ ID NO:15)

GGTCACAAAGGCATTGGAGGCAATACCGAGGCTGACGAAGGAGTGAAGAA

AGCCCTGGAGCAAATGGCACCATGTTCCCCTCCCGAGGCTATCCTGCTCA

TAAACCTGGCGAGAAGCAAAACCTGGAGACCGGCATCTACATGCAAGGCC

TGAGACCTCAGAGCTTCCTGCCCCGCGCTGACCTCCCTGTCGCAATCACT

GGCACCATGGTGGACTCCGAGCTGCAGCTCCAACTGCTGAACATCGGCAC

CGAGCACATTCGCATCCAGAAGGACGAGGTGTTCATGACATGCTTCCTGG

AGAACATCCCTAGCGCCACCGAAGACCACGAGAGATGGCACACATCCCCA

GACATCCTGGTCCGCCAGTTCCACCTGCCCAAGCGCATCGCCAAGGAGAT

CGTCGCCCGCTGCCAGGAGTGCAAGAGAACCACAACCTCCCCAGTGCGCG

GCACCAACCCTAGAGGACGCTTCCTGTGGGAGATGGACAACACACACTGG

AACAAAACCATCATTTGGGTCGCAGTGGAGACTAACAGCGGACTGGTGGA

GGCTCAGGTGATTCCCGAAGAGACCGCACTGCAAGTGGCCCTGTGTATCC

TCCAGCTGATCCAACGCTACACCGTCCTGCACCTGCACAGCGACAACGGA

CCCTGCTTCACAGCTCACCGCATCGAGAACCTGTGCAAGTACCTGGGGAT

CACCAAGACAACCGGCATTCCCTACAATCCTCAGAGCCAAGGAGTCGTGG

AAAGAGCCCATCGCGACCTGAAGGACAGACTGGCTGCCTATCAAGGCGAC

TGCGAGACCGTGGAAGCTGCACTGAGCCTCGCCCTGGTCAGCCTGAACAA

GAAGAGAGGAGGCATCGGCGGACACACACCCTACGAGATCTATCTGGAGA

GCGAGCACACCAAGTATCAGGACCAACTGGAGCAGCAATTCAGCAAGCAG

AAGATCGAGAAATGGTGCTACGTCCGCAACAGACGCAAGGAGTGGAAGGG

CCCTTACAAGGTGCTGTGGGATGGCGACGGAGCTGCAGTGATCGAGGAAG

AGGGCAAGACCGCTCTGTATCGCCACCGGCACATGCGCTTCATCCCACCT

CCCGACAGCGATATCCAGGACGGCTCCAGCTGA

TABLE 5

| Packaging Construct | Transduction Efficiency | Mean GFP Intensity |
|---|---|---|
| Mock | 0% | 0 |
| pCligpSyn | 91% | 1000 |
| pCligpSynSer | 92% | 1050 |

Comparison of BIV vector mediated GFP expression in HeLa cells. BIV vectors encoding GFP was generated either by the packaging construct, pCligpSyn or by the packaging construct, pCligpSynSer were compared for their transduction efficiencies of HeLa cells and intensity of GFP expression. Transduction efficiency was measured by the percentage of the positive HeLa cells. Mean GFP intensity was scored by relative fluorescence intensity. Both transduction efficiency and mean GFP intensity were analyzed by flow cytometry analysis on a FACS Calibur (Becton Dickinson Biosciences).

We have proposed in this application that a mutation in the BIV protease coding region reduces the toxicity of the BIV protease to the cells. Specifically, a point mutation is made in the packaging construct pCligpSyn at the amino acid Thr coded by nucleotides ACT (corresponding to nucleotides from 1806 to 1808 in BIV viral genomic RNA isolate 127, Garvey et al., 1990). The said Thr will be replaced with Ser at the same position without any change in any other coding region of the packaging construct. This packaging construct with a Thr to Ser mutation was designated as pCligpSynSer. pCligpSynSer was compared to pCligpSyn for the ability to support BIV vector production and the transduction efficiency achieved by the BIV vectors. Specifically, $8 \times 10^6$ 293T cells in 10-CM dishes were transfected with pCligpSyn or pCligpSynSer (1 ug), pTracerARev (10 ug), pBIVminivec (15 ug), and pCMVVSV-G (4.5 ug). Forty-eight hours after transfection, vectors were harvested from the transfected cells. HeLa cells were transduced with equal numbers of vector particles as indicated by reverse transcriptase (RT) activity. Forty-eight hours after transduction, flow cytometry analysis was performed to score GFP positive HeLa cells. As indicated in Table 5, the vector generated by the packaging construct with the Thr to Ser mutation, pCligpSynSer transduced HeLa cells as efficiently as the vector produced by the packaging construct pCligpSyn. The nucleotide sequence for this mutated gag/pol gene is shown in Table 6 (SEQ ID NO:17).

TABLE 6

Sequence of recoded gag/pol with protease mutation (Seq ID:17)

ATGAAGCGGAGAGAGCTGGAGAAGAAACTGAGGAAAGTGCGCGTGACACC

TCAACAGGACAAGTACTATACCATCGGCAACCTGCAGTGGGCCATCCGCA

TGATCAACCTGATGGGCATCAAGTGCGTGTGCGACGAGGAATGCAGCGCC

GCTGAGGTCGCCCTGATCATCACCCAGTTTAGCGCCCTCGACCTGGAGAA

CTCCCCTATCCGCGGCAAGGAAGAGGTGGCCATCAAGAATACCCTGAAGG

TGTTTTGGAGCCTGCTGGCCGGATACAAGCCTGAGAGCACCGAGACCGCC

CTGGGATACTGGGAAGCCTTCACCTACAGAGAGAGGGAAGCTAGAGCCGA

CAAGGAGGGAGAGATCAAGAGCATCTACCCTAGCCTGACCCAGAACACCC

AGAACAAGAAACAGACCAGCAATCAGACAAACACCCAGAGCCTGCCCGCT

ATCACCACACAGGATGGCACCCCTCGCTTCGACCCCGACCTGATGAAGCA

GCTGAAGATCTGGTCCGATGCCACAGAGCGCAATGGAGTGGACCTGCATG

CCGTGAACATCCTGGGAGTGATCACAGCCAACCTGGTGCAAGAAGAGATC

AAGCTCCTGCTGAATAGCACACCCAAGTGGCGCCTGGACGTGCAGCTGAT

CGAGAGCAAAGTGAGAGAGAAGGAGAACGCCCACCGCACCTGGAAGCAGC

ATCACCCTGAGGCTCCCAAGACAGACGAGATCATTGGAAAGGGACTGAGC

TCCGCCGAGCAGGCTACCCTGATCAGCGTGGAGTGCAGAGAGACCTTCCG

CCAGTGGGTGCTGCAGGCTGCCATGGAGGTCGCCCAGGCTAAGCACGCCA

CACCCGGACCTATCAACATCCATCAAGGCCCTAAGGAACCCTACACCGAC

TTCATCAACCGCCTGGTGGCTGCCCTGGAAGGAATGGCCGCTCCCGAGAC

CACAAAGGAGTACCTCCTGCAGCACCTGAGCATCGACCACGCCAACGAGG

ACTGTCAGTCCATCCTGCGCCCTCTGGGACCCAACACACCTATGGAGAAG

AAACTGGAGGCCTGTCGCGTGGTGGGAAGCCAGAAGAGCAAGATGCAGTT

CCTGGTGGCCGCTATGAAGGAAATGGGGATCCAGTCTCCTATTCCAGCCG

TGCTGCCTCACACACCCGAAGCCTACGCCTCCCAAACCTCAGGGCCCGAG

GATGGTAGGAGATGTTACGGATGTGGGAAGACAGGACATTTGAAGAGGAA

TTGTAAACAGCAAAAATGCTACCATTGTGGCAAACCTGGCCACCAAGCAA

GAAACTGCAGGTCAAAAAACGGGAAGTGCTCCTCTGCCCCTTATGGGCAG

AGGAGCCAACCACAGAACAATTTTCACCAGAGCAACATGAGTTCTGTGAC

CCCATCTGCACCCCCTCTTATATTAGATTAGACAAACAGCCTTTTATAAA

TABLE 6-continued

Sequence of recoded gag/pol with protease mutation (Seq ID:17)

GGTGTTCATTGGCGGCCGCTGGGTGAAGGGACTGGTGGACTCAGGCGCTG

ACGAGGTGGTGCTGAAGAACATCCACTGGGACCGCATCAAAGGCTACCCT

GGAACACCCATCAAGCAGATCGGCGTGAACGGCGTGAACGTGGCTAAGCG

CAAAACACATGTGGAGTGGAGATTCAAAGACAAGACCGGCATCATTGACG

TCCTCTTCAGCGACACACCTGTGAACCTGTTTGGCAGAAGCCTGCTCAGA

TCCATCGTGACCTGCTTTACCCTGCTGGTGCACACCGAGAAGATCGAGCC

ACTGCCTGTGAAGGTGCGCGGCCCTGGACCTAAGGTGCCACAATGGCCCC

TGACCAAGGAGAAATACCAGGCCCTGAAGGAGATCGTGAAGGACCTGCTG

GCCGAGGGAAAGATCAGCGAAGCTGCCTGGGACAACCCTTACAACACACC

CGTGTTCGTGATCAAGAAGAAAGGCACCGGCCGCTGGCGCATGCTGATGG

ACTTCCGCGAGCTGAATAAGATCACCGTGAAAGGCCAAGAGTTCAGCACA

GGACTCCCTTATCCACCCGGCATCAAGGAGTGTGAGCACCTGACCGCCAT

CGACATCAAGGACGCCTACTTCACCATCCCTCTGCACGAGGACTTCAGAC

CCTTCACAGCCTTCAGCGTGGTCCCAGTGAACCGCGAGGGCCCCATCGAG

CGGTTCCAGTGGAACGTCCTGCCTCAAGGCTGGGTGTGCTCCCCTGCCAT

CTACCAGACCACAACCCAGAAGATCATTGAGAACATCAAGAAGAGCCATC

CCGACGTGATGCTGTATCAGTACATGGATGACCTCCTGATTGGCAGCAAT

CGCGATGACCACAAGCAGATCGTGCAGGAGATCAGAGACAAGCTGGGCAG

CTATGGCTTCAAGACACCCGACGAGAAAGTGCAGGAAGAGCGCGTGAAGT

GGATCGGCTTCGAGCTGACACCTAAGAAATGGAGATTCCAGCGTAGGCAA

CTGAAGATCAAGAACCCACTGACCGTGAACGAACTCCAGCAGCTGGTCGG

CAACTGTGTGTGGGTGCAGCCCGAGGTGAAGATCCCTCTGTACCCACTGA

CCGATCTGCTCCGCGACAAGACCAACCTGCAGGAAAAGATCCAGCTGACA

CCCGAGGCCATCAAGTGCGTGGAAGAGTTCAACCTGAAGCTGAAAGATCC

CGAGTGGAAGGACAGAATTCGCGAAGGAGCCGAGCTGGTGATCAAGATCC

AAATGGTCCCTCGCGGCATCGTGTTCGACCTGCTGCAAGACGGCAATCCT

ATCTGGGAGGCGTGAAAGGACTGAACTACGACCACAGCAACAAGATCAA

GAAGATCCTGCGCACCATGAACGAGCTGAACCGCACCGTGGTGATCATGA

CCGGACGCGAAGCTAGCTTTCTCCTGCCTGGATCCAGCGAGGATTGGGAG

GCCGCCCTGCAGAAGGAAGAGAGCCTGACCCAAATCTTTCCCGTGAAGTT

CTACCGCCATAGCTGTAGATGGACAAGCATCTGTGGACCCGTCCGCAGAG

ACCTGACCACCTACTATACCGACGGCGGGAAGAAAGGAAAGACAGCTGCG

GCAGTGTACTGGTGTGAAGGAAGAACTAAGAGCAAAGTGTTCCCTGGAAC

CAATCAACAGGCTGAGCTGAAGGCAATCTGCATGGCTCTGCTGGACGGAC

CTCCCAAGATGAACATCATCACCGACAGCCGCTACGCTTATGAGGGCATG

AGAGAGGAACCTGAGACCTGGGCTCGCGAGGGCATCTGGCTGGAGATTGC

AAAGATCCTGCCATTCAAGCAATACGTCGGAGTGGGCTGGGTCCCTGCTC

ACAAAGGCATTGGAGGCAATACCGAGGCTGACGAAGGAGTGAAGAAAGCC

CTGGAGCAAATGGCACCATGTTCCCCTCCCGAGGCTATGCTGCTCAAACC

TGGCGAGAAGCAAAACCTGGAGACCGGCATCTACATGCAAGGCCTGAGAC

CTCAGAGCTTCCTGCCCCGCGCTGACCTCCCTGTCGCAATCACTGGCACC

ATGGTGGACTCCGAGCTGCAGCTCCAACTGCTGAACATCGGCACCGAGCA

CATTCGCATCCAGAAGGACGAGGTGTTCATGACATGCTTCCTGGAGAACA

TCCCTAGCGCCACCGAAGACCACGAGAGATGGCACACATCCCCAGACATC

CTGGTCCGCCAGTTCCACCTGCCCAAGCGCATCGCCAAGGAGATCGTCGC

CCGCTGCCAGGAGTGCAAGAGAACCACAACCTCCCCAGTGCGCGGCACCA

ACCCTAGAGGACGCTTCCTGTGGCAGATGGACAACACACACTGGAACAAA

ACCATCATTTGGGTCGCAGTGGAGACTAACAGCGGACTGGTGGAGGCTCA

GGTGATTCCCGAAGAGACCGCACTGCAAGTGGCCCTGTGTATCCTCCAGC

TGATCCAACGCTACACCGTCCTGCACCTGCACAGCGACAACGGACCCTGC

TTCACAGCTCACCGCATCGAGAACCTGTGCAAGTACCTGGGCATCACCAA

GACAACCGGCATTGCCTACAATCCTCAGAGCCAAGGAGTCGTGGAAAGAG

CCCATCGCGACGTGAAGGACAGACTGGCTGCCTATCAAGGCGACTGCGAG

ACCGTGGAAGCTGCACTGAGCCTCGCCCTGGTCAGCCTGAACAAGAAGAG

AGGAGGCATCGGCGGACACACCACCCTACGAGATCTATCTGGAGAGCGAGC

ACACCAAGTATCAGGACCAACTGGAGCAGCAATTCAGCAAGCAGAAGATC

GAGAAATGGTGCTACGTCCGCAACAGACGCAAGGAGTGGAAGGGCCCTTA

CAAGGTGCTGTGGGATGGCGACGGAGCTGCAGTGATCGAGGAAGAGGGCA

AGACCGCTCTGTATCCCCACCGGCACATGCGCTTCATCCCCACCTCCCGAC

AGCGATATCCAGGACGGCTCCAGCTGA

TABLE 7

Sequence of Rev gene (SEQ ID NO:16)

ATGGATCAGGACCTAGACCGCGCGGAACGCGGGGAAAGGGGAGGAGGATC

CGAAGAACTGCTTCAGGAGGAGATCAACGAAGGGAGGCTGACAGCCAGAG

AAGCTTTACAAACATGGATCAATAACGATTCTCCTAGGTATGTTAAGAAG

CTGCGCCAAGGTCAGGCAGAATTACCAACATCTCCCGGCGGAGGAGGAGG

ACGGGGACACAGAGCCAGAAAGCTCCCCGGCGAGAGGAGACCCGGCTTCT

GGAAGTCTCTACGAGAATTGGTTGAACAAAATAGGAGAAAGCAAGAACGA

CGCCTATCGGGTCTGGACAGAAGAATACAACAGCTTGAGGATCTTGTTCG

CCACATGTCGCTGGGATCTCCTGACCCCTCAACTCCTTCAGCTTGCGTTC

TTTCTGTTAACCCTGCTGCTCAAACTCCTTTGGGACATCTTCCGCCACGC

TCCTATTTTAAACTTAAAAGGGTGGACTGTGGGCAGGGTGGGACCTCAG

GACAACAGCAGCCCCGGACTTCCCATATGTGAATTGGACTGGATCCAGG

GAACAAATAA

Example 10

One Method for Generation of Producer Cell Lines for BIV Based Lentiviral Vectors The BIV based lentiviral packaging construct pCIBIVGP-mut is transfected into 293Ea6 cells (a cell line expressing A-MLV envelope as described in this invention in Example 3) together with a plasmid encoding selectable marker puromycin as described in this invention for HIV based lentiviral packaging construct. The transfected cells are cultured in a medium containing puromycin as described in this invention in Example 3. The puromycin resistant single cell clones are monitored for BIV Gag/Pol production in the cell culture medium by specifically assaying for BIV Reverse Transcriptase (RT) activity. The RT assay is performed with a RT assay Kit purchased from Roche (Product No: 1828657) by taking advantage of the fact that BIV RT cross-reacts with HIV RT. Single cell clone expressing the highest RT is monitored for its stability in BIV Gag/Pol production. Alternatively, other mammalian cell lines instead of 293 cell line is used. Alternatively, a cell line constitutively expressing other viral envelope instead of A-MLV envelope is used. A BIV based transfer vector is introduced into the cell clone with highest stable production of BIV RT through transfection with a BIV based transfer vector plasmid or infection with a BIV based lentiviral vector particles. Supernatants resulting from the packaging cell line are collected at various times.

Example 11

Another Method for Generation of Producer Cell Lines for BIV Based Lentiviral Vectors To generate a producer cell line for BIV-based lentiviral vector production, a construct encoding recoded BIV Gag/Pol with the protease mutation is co-transfected with a plasmid encoding the selectable marker hygromycin into 293 cells. Hygromycin resistant clones are selected and screened for BIV Gag/Pol expression by reverse transcriptase (RT) activity assay. Positive clones expressing BIV Gag/pol are expanded for functional analysis by co-transfection with BIV Rev expression construct (pTracerARev), VSV-G expression construct, and a BIV transfer vector construct encoding GFP. Forty-eight hours after transfection, supernatant from the transfected cells is collected and used to transduce naïve 293 cells.

The clones producing the highest amounts of functional BIV vectors as indicated by the percentage of GFP positive cells are saved for further use. To the identified functional cell clones that express BIV Gag/Pol, a second construct encoding BIV Rev with a selectable marker puromycin (pEF1aRevIRESPuro) is introduced by transfection. Puromycin resistant clones are selected. The clones are then screened for functional BIV Gag/Pol and Rev expression by co-transfection with a VSV-G expression construct and a BIV transfer vector construct encoding GFP. Forty-eight hours after transfection, supernatant from the transfected cells will be collected and used to transduce naïve 293 cells. The clones producing the highest amounts of functional BIV vectors as indicated by the percentage of GFP positive cells are saved for further use. To the functional cell clones that express BIV Gag/pol and BIV Rev, a third construct encoding mutant LCMV glycoprotein (Beyer et al., *J. Virol.* 76:1488-1495) with a selectable marker neomycin (pCILCMVgpIRESNeo) is introduced by transfection. Neomycin (G418) resistant clones are selected. The clones are then screened for functional BIV Gag/Pol, BIV Rev, and mutant LCMV glycoprotein expression by transfection with a BIV transfer vector construct encoding GFP. The clones producing the highest amounts of functional BIV vectors as indicated by the percentage of GFP positive cells are saved for further use. The identified clones simultaneously expressing functional BIV Gag/Pol, BIV Rev, and mutant LCMV glycoprotein serve as a packaging cell line. To generate a producer cell line for a given BIV-based vector production, a BIV-based transfer vector encoding a desired transgene (marker gene or therapeutic gene) is introduced into the packaging cell line through transfection with a BIV-based transfer vector plasmid or infection with a BIV-based lentiviral vector particle. Supernatant obtained from the packaging cell line contains the desired BIV-based lentiviral vector.

The invention claimed is:

1. A method for producing a recombinant lentiviral vector particle preparation comprising the steps of:
   transfecting a packaging cell line comprising a packaging construct comprising a sequence encoding a lentiviral protease containing a substitution where T is replaced with S in the DTGAD motif (SEQ ID NO: 1) and a deletion in a lentiviral packaging signal sequence with a lentiviral vector,
   propagating the cell line in a suitable culture medium and obtaining a recombinant lentiviral vector particles preparation from said culture medium.

2. The method of claim 1, wherein said sequence encoding said protease comprises a lentiviral pol gene.

3. The method of claim 2, further comprising a lentiviral gag gene.

4. The method of claim 1 wherein said lentiviral protease is an HIV protease.

5. The method of claim 1 wherein said lentiviral protease is a BIV protease.

6. The method of claim 1 wherein said lentiviral protease is an EIAV protease.

7. The method of claim 1 wherein said lentiviral protease is an SIV protease.

8. The method of claim 1 wherein said lentiviral protease is an FIV protease.

9. The method of claim 1 wherein expression of the lentiviral protease gene is constitutive.

10. The method of claim 1 wherein said cell line further comprises an env gene.

11. The method of claim 1, 2 or 3, wherein said sequence encoding a lentiviral protease is obtained from HIV genome.

12. The method of claim 1, 2 or 3, wherein said sequence encoding a lentiviral protease is obtained from BIV genome.

13. The method of claim 1 wherein expression of the lentiviral gag gene is constitutive.

14. The method of claim 2 or 3 wherein expression of the lentiviral pol gene is constitutive.

15. The method of claim 11 further comprising a deletion of, or mutation in, a vif gene, a vpr gene or both.

16. The method of claim 12 further comprising a deletion of, or mutation in, one or more of a vif gene, a W gene, a Y gene or a Tat gene.

17. The method of claim 1 or 10, wherein said cell line further comprises a rev gene.

* * * * *